US009677125B2

(12) United States Patent
Sood et al.

(10) Patent No.: US 9,677,125 B2
(45) Date of Patent: Jun. 13, 2017

(54) DETECTION OF PLURALITY OF TARGETS IN BIOLOGICAL SAMPLES

(75) Inventors: Anup Sood, Clifton Park, NY (US); John Richard Nelson, Clifton Park, NY (US); Michael John Gerdes, Albany, NY (US)

(73) Assignee: General Electric Company, Niskayuna, NY (US)

( * ) Notice: Subject to any disclaimer, the term of this patent is extended or adjusted under 35 U.S.C. 154(b) by 643 days.

(21) Appl. No.: 12/582,745

(22) Filed: Oct. 21, 2009

(65) Prior Publication Data

US 2011/0092381 A1    Apr. 21, 2011

(51) Int. Cl.
C12Q 1/68    (2006.01)

(52) U.S. Cl.
CPC ..... *C12Q 1/6816* (2013.01); *C12Q 2600/158* (2013.01)

(58) Field of Classification Search
None
See application file for complete search history.

(56) References Cited

U.S. PATENT DOCUMENTS

| | | |
|---|---|---|
| 4,405,720 A | 9/1983 | Merril |
| 5,401,469 A | 3/1995 | Kobayashi et al. |
| 5,571,643 A | 11/1996 | Martin et al. |
| 5,756,709 A | 5/1998 | Nelson et al. |
| 5,763,152 A | 6/1998 | Hioki et al. |
| 5,776,755 A | 7/1998 | Alitalo et al. |
| 5,807,522 A | 9/1998 | Brown et al. |
| 5,827,656 A | 10/1998 | Nelson et al. |
| 5,830,645 A | 11/1998 | Pinkel et al. |
| 6,083,486 A | 7/2000 | Weissleder et al. |
| 6,150,173 A | 11/2000 | Schubert et al. |
| 6,391,649 B1 | 5/2002 | Chait et al. |
| 6,534,041 B1 | 3/2003 | Licha et al. |
| 6,573,043 B1 | 6/2003 | Cohen et al. |
| 6,635,435 B1 | 10/2003 | Conrad et al. |
| 6,696,246 B1 | 2/2004 | Huan et al. |
| 6,833,246 B2 | 12/2004 | Balasubramanian et al. |
| 6,924,115 B2 | 8/2005 | Schubert et al. |
| 7,629,125 B2 | 12/2009 | Sood et al. |
| 8,304,195 B2 | 11/2012 | Hagen et al. |
| 2001/0039023 A1 | 11/2001 | Schubert |
| 2002/0106648 A1 | 8/2002 | Lizardi et al. |
| 2002/0114742 A1 | 8/2002 | Takahashi et al. |
| 2002/0116132 A1 | 8/2002 | Rhett et al. |
| 2002/0173053 A1 | 11/2002 | Damaj et al. |
| 2002/0177149 A1 | 11/2002 | Rimm et al. |
| 2003/0044353 A1 | 3/2003 | Weissleder et al. |
| 2003/0064398 A1 | 4/2003 | Barnes et al. |
| 2003/0073149 A1 | 4/2003 | Archer et al. |
| 2003/0211458 A1 | 11/2003 | Sunray et al. |
| 2004/0009499 A1 | 1/2004 | Tomita et al. |
| 2004/0121352 A1 | 6/2004 | Dale |
| 2004/0121382 A1 | 6/2004 | Liu et al. |
| 2004/0248325 A1 | 12/2004 | Bukusoglu et al. |
| 2005/0169543 A1 | 8/2005 | Damera-Venkata |
| 2005/0169843 A1 | 8/2005 | Weissleder et al. |
| 2005/0171434 A1 | 8/2005 | Madden et al. |
| 2005/0233437 A1 | 10/2005 | Kureshy et al. |
| 2008/0118944 A1 | 5/2008 | Larsen et al. |
| 2010/0120043 A1 | 5/2010 | Sood et al. |
| 2012/0231967 A1 | 9/2012 | Sood et al. |
| 2012/0252685 A1 | 10/2012 | Treynor et al. |

FOREIGN PATENT DOCUMENTS

| | | |
|---|---|---|
| CN | 1313908 A | 9/2001 |
| DE | 4421891 C2 | 1/1996 |
| DE | 10143757 A1 | 3/2003 |
| EP | 153873 A2 | 9/1985 |
| EP | 0801306 A1 | 10/1997 |
| EP | 1950566 A1 | 7/2008 |
| FR | 2711671 A1 | 5/1995 |
| JP | 10503841 A | 4/1998 |
| JP | 11510681 A | 9/1999 |
| JP | 2000009732 A | 1/2000 |
| JP | 2002520448 A | 7/2002 |
| JP | 2002527404 A | 8/2002 |
| JP | 2002323416 A | 11/2002 |
| JP | 2002350431 A | 12/2002 |
| JP | 2003533209 A | 11/2003 |
| JP | 2004041121 A | 2/2004 |
| JP | 2005083942 A | 3/2005 |
| JP | 2005261236 A | 9/2005 |
| JP | 2006042641 A | 2/2006 |
| JP | 2006513398 A | 4/2006 |
| JP | 2007033159 A | 2/2007 |

(Continued)

OTHER PUBLICATIONS

Whalby et al (2001 Proceedings of SCIA Bergen, Norway).*
Walter Schubert, Bernd Bonnekoh, Ansgar J Pommer, Lars Philipsen, Raik BoCkelmann, Yanina Malykh, Harald Gollnick, Manuela Friedenberger, Marcus Bode and Andreas W M Dress; "Analyzing proteome topology and function by automated multi-dimensional fluorescence microscopy"; Received Feb. 1; accepted Aug. 16; published online Oct. 1, 2006; doi:10.1038/nbt1250; 9 Pages.
Segan et al; "Decomposition of Pinacyanol Chloride Dye Using Several Manganese Oxide Catalysts", Chem. Mater, vol. 9, pp. 2526-2532 (1997).
Wahlby et al.; "Sequential immunofluorescence staining and image analysis for detection of large number of antigens in individual cell nuclei", Cytometry vol. 47, pp. 32-41 (2002).

(Continued)

*Primary Examiner* — Christopher M Gross
(74) *Attorney, Agent, or Firm* — Pabitra K. Chakrabarti

(57) ABSTRACT

Methods for detecting a plurality of targets in a biological sample are provided. The method comprises contacting the biological sample with a plurality of target-binding probes to form a plurality of target-bound probes, covalently attaching at least one of the target-bound probes to the biological sample, and observing the signals from the target-bound probes sequentially. An associated kit and device for detection of the plurality of targets are also provided.

11 Claims, 7 Drawing Sheets

(56) References Cited

FOREIGN PATENT DOCUMENTS

| JP | 2010520989 A | | 6/2010 |
|---|---|---|---|
| WO | 9409022 A1 | | 4/1994 |
| WO | 9503428 A1 | | 2/1995 |
| WO | 9708343 A1 | | 3/1997 |
| WO | 9802577 A1 | | 1/1998 |
| WO | 0003034 A2 | | 1/2000 |
| WO | 0008507 A2 | | 2/2000 |
| WO | WO 00/14281 | * | 3/2000 |
| WO | 0020641 A1 | | 4/2000 |
| WO | 0058507 A1 | | 10/2000 |
| WO | 02079771 A1 | | 10/2002 |
| WO | 03073149 A1 | | 9/2003 |
| WO | 2005017485 A2 | | 2/2005 |
| WO | 2007055302 A1 | | 5/2007 |
| WO | 2008064067 A2 | | 5/2008 |
| WO | 2008133729 A2 | | 11/2008 |

OTHER PUBLICATIONS

Mittag et al.; "Sequential photobleaching of fluorochromes for polychromatic slide-based cytometry", Cytometry Part A, vol. 69A, pp. 139-141 (2006).

Laffers et al.; "Iterative restaining as a pivotal tool for n-color immunophenotyping by lside-based cytometry", Cytometry Part A, vol. 69A, pp. 127-130 (2006).

PCT/EP2010/065876 Search Report and Written Opinion, Feb. 7, 2011.

Unofficial English translation of Office Action issued in connection with corresponding CN Application No. 201080058305.8 on Jul. 1, 2013.

Walter Schubert, "Multiple Antigen-Mapping Microscopy of Human Tissue", p. 97-98, 1990, Advances in Analytical Cellular Pathology, Proceedings of the first Conference of the European Society for Analytical Cellular Pathology, Schloss Elmau, F.R.G., Nov. 12-17, 1989, Excerpta Medica, Amsterdam, New York, Oxford, Published by Elsevier Science Publishers B.V.

Rene "Methods of immunological analysis",VCH Verlagsgesellschaft MBH, vol. 3, pp. 318-319, 1993.

Press et al., "Amplification and Overexpression of HER-2/neu in Carcinomas of the Salivary Gland: Correlation With Poor Prognosis1", Cancer Research, vol. 54, pp. 5675-5682, Nov. 1, 1994.

Ratcliffe et al., "The Combination of In Situ Hybridization and Immunohistochemical Analysis: An Evaluation of Her2/neu Expression in Paraffin-Embedded Breast Carcinomas and Adjacent Normal-Appearing Breast Epithelium", Modern Pathology, vol. 10, No. 12, pp. 1247-1252, 1997.

Gardiner et al., "Development of a Technique that Allows Simultaneous Assessment of the Morphology and Gene Amplification by FISH: Application to HER-2/Neu Amplification in Breast Cancer", Modern Pathology. vol. 12, No. 1, p. 191A and cover sheet, Jan. 1999, Abstract.

Gharahdaghi et al., "Mass Spectrometric Identification of Proteins From Silver-Stained Polyacrylamide Gel: A Method for the Removal of Silver Ions to Enhance Sensitivity", Electrophoresis, vol. 20, pp. 601-605, 1999.

Kajtar et al., "Automated Fluorescent In Situ Hybridization (FISH) Analysis of t(9:22)(q34;q11) in Interphase Nuclei", Cytometry A, vol. 69, No. 6, pp. 506-514, Jun. 1, 2006.

Walter Schubert et al., "Analyzing proteome topology and function by automated multidimensional fluorescence microscopy", Nature Biotechnology, 2006, 24, pp. 1-9.

* cited by examiner

SAMPLE 1

SAMPLE 2

SAMPLE 3

DETECTION OF PLURALITY OF TARGETS IN BIOLOGICAL SAMPLES

FIELD OF INVENTION

The invention generally relates to methods, kits and devices for detecting a plurality of targets in a biological sample.

BACKGROUND

Analysis of a biological sample to discern its characteristics, and to get information about various biological targets is in demand both in biology and medicine. A variety of methods may be employed for analyzing the biological sample to detect, inter alia, the presence, absence, concentration, and/or spatial distribution of the biological targets. For example, detection of proteins in histological sections or cytological preparations may be performed using histochemistry, immunohistochemistry (IHC), or immunofluorescence.

However, many of the existing techniques for detecting targets in a biological sample have limitations in terms of sensitivity, accuracy and/or multiplexing abilities. Particularly, detection of multiple targets in a single biological sample is often limited to the detection of only a few targets (about 4 to 5 targets) at a time. For example, the number of targets that are accurately detectable in a single tissue sample during an immunofluorescence assay is limited by the sensitivity of florescence-based detection system to resolve overlapping signals. Hence, additional biological samples from the source may often be required to get information about all the relevant targets.

Analysis of multiple biological samples limits the ability to accurately determine relative characteristics (e.g., the presence, absence, concentration, and/or spatial distribution) of a plurality of different targets in the biological sample. Moreover, in certain instances, a limited amount of sample may only be available for analysis. Thus, methods, agents, and devices capable of analyzing an individual biological sample to detect a plurality of different targets in the biological sample are needed.

BRIEF DESCRIPTION

The methods for detecting a plurality of targets in a biological sample generally comprise the steps of contacting the biological sample with a plurality of target-binding probes to form a plurality of target-bound probes, covalently attaching at least one of the target-bound probes to the biological sample, and observing a first set of signals from a first set of the plurality of target-bound probes. The methods further comprise the steps of modifying the observed signals followed by generating a second set of signals from a second set of the plurality of target-bound probes, and observing the second set of signals.

Additional examples of the methods for detecting a plurality of targets in a biological sample generally comprise the steps of contacting the biological sample with a plurality of target-binding probes to form a plurality of target-bound probes, covalently attaching at least one of the target-bound probes to the biological sample, generating a first set of signals from a first set of the plurality of target-bound probes, and observing the first set of signals. The methods further comprise the steps of modifying the observed signals, generating a second set of signals from a second set of the plurality of target-bound probes, and observing the second set of signals.

Other examples of the methods for detecting a plurality of targets in a biological sample comprise the steps of contacting the biological sample with a plurality of target-binding probes to form a plurality of target-bound probes, covalently attaching at least one of the target-bound probes to the biological sample, contacting the target-bound probes with a first set signal-generating probes that are capable of binding a first set of the plurality of target-bound probes, and are capable of generating a first set of signals, and detecting the first set of the plurality of targets via observing the first set of signals. The method further comprises the steps of modifying the observed first set of signals. The contacting steps, the detecting step, and the modifying step may be repeated multiple times using a subsequent set of signal-generating probes to detect a subsequent set of the plurality of targets, wherein the subsequent set of signal-generating probes are capable of binding a subsequent set of the plurality of target-bound probes, and are capable of generating a subsequent set of signals.

The kits for detection of a plurality of multiple targets in a biological sample generally comprise a plurality of target-binding probes, wherein each target-binding probe is capable of generating a signal, and at least one chemical agent that is capable of modifying the generated signal from at least one target-binding probe. At least one of the plurality of target-binding probes is further capable of cross-linking to a target or to a molecule that is located in the vicinity of the target.

The devices for detection of a plurality of targets in a biological sample generally comprise a sample handling system, a reagent dispensing system, a probe cross-linking system, and a signal detection system.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
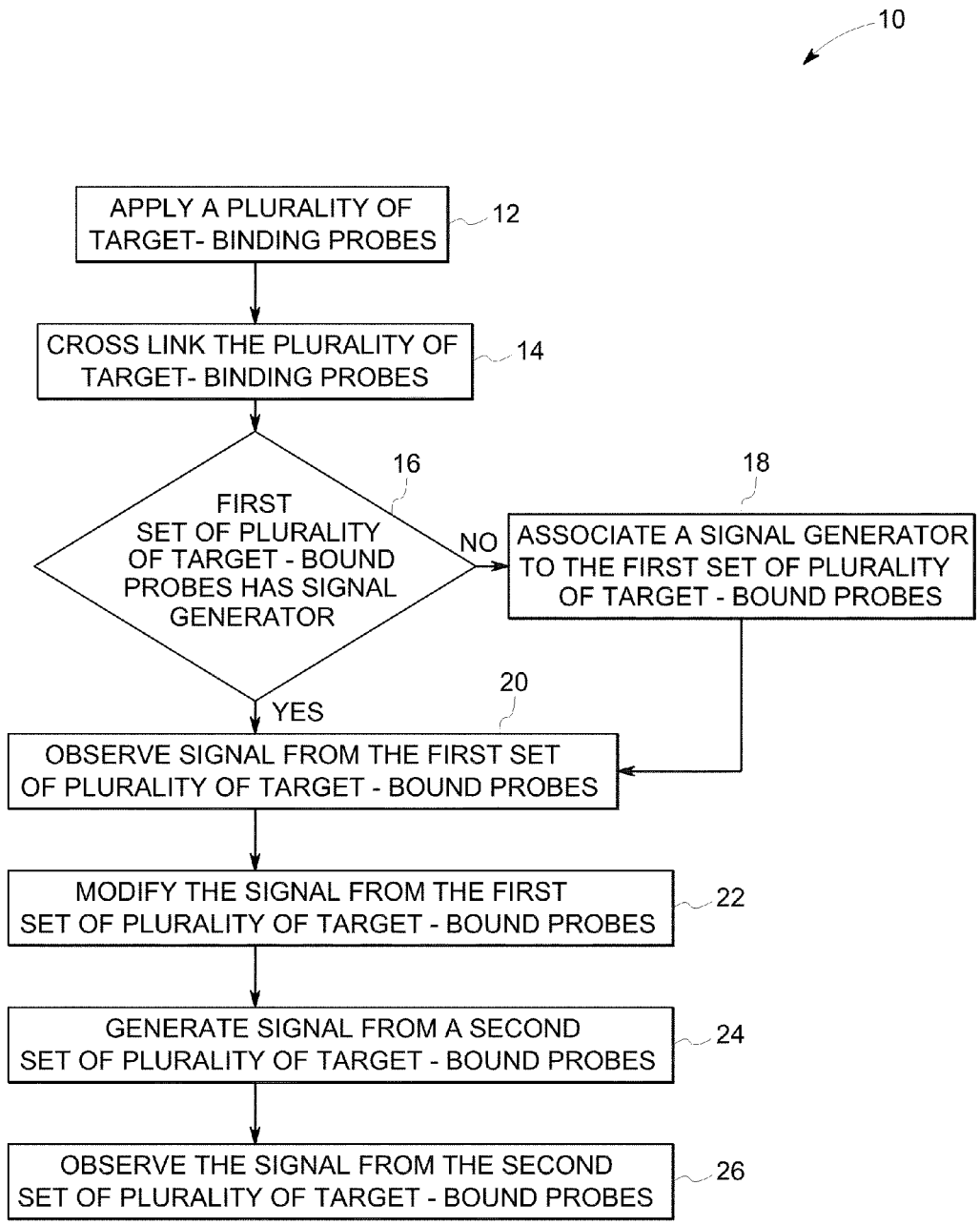
FIG. 1 is a flow diagram illustrating an embodiment of the invention.

To more clearly and concisely describe, and point out the subject matter of the claimed invention, the following definitions are provided for specific terms, which are used in the following description and the appended claims. Throughout the specification, exemplification of specific terms should be considered as non-limiting examples.

The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Similarly, "free" may be used in combination with a term, and may include an insubstantial number, or trace amounts while still being considered free of the modified term. Where necessary, ranges have been supplied, and those ranges are inclusive of all sub-ranges there between.

The term "biological sample," as used herein, refers to a sample of biological origin, or a sample derived from the sample of biological origin. Biological sample may be an in vivo sample or an in vitro sample. Biological sample may be of prokaryotic origin or eukaryotic origin. For example, the biological sample may be originated from a biological subject such as a bacterium, a fungus, a protozoan, an insect, a fish, a bird, a reptile, a mammal (e.g., mouse, rat, cow, dog, donkey, guinea pig, or rabbit), or a primate (e.g., chimpanzee, or human).

Biological sample may be obtained or derived from a biological subject by a variety of methods. For example, a biological sample may include tissues or cells isolated from mammals (e.g., humans), sections of a biological sample (e.g., sectional portion of an organ or tissue), or extracts from a biological sample (e.g., an antigen extracted from a body fluid such as blood, blood plasma, serum, or urine). Non-limiting examples of the biological sample include, cells, cell fragments, tissues, tissue sections, organs, or body fluids. The biological sample may be immobilized on a solid support such as in blots or arrays. For example, the biological sample may be immobilized on a membrane, a paper, a glass slide, a microtiter plate, or an ELISA plate.

The term "nucleic acid" is meant to include any deoxyribonucleic acid (DNA), ribonucleic acid (RNA) (e.g., a chromosomal, a mitochondrial, a viral, or a bacterial nucleic acid), or their analogues. The term "nucleic acid" encompasses either strand or both strands of a double stranded nucleic acid molecule. The nucleic acid may be a natural nucleic acid or a synthetic nucleic acid.

The term "target," as used herein, generally refers to a component (e.g., a biological molecule such as a protein or a nucleic acid, a part of a biological molecule such as an epitope, or a biological structure) of a biological sample that may be detected or analyzed when present in the biological sample. The target may be any substance for which there exists a naturally occurring target-binding moiety (e.g., an antibody to a target antigen), or for which a target-binding moiety may be prepared (e.g., a synthetic small molecule binder such as a ligand for a target receptor). Non-limiting examples of suitable targets include peptides, proteins, oligonucleotides, nucleic acids (e.g., DNA or RNA), polysaccharides (e.g., lectins or sugars), lipids, ligands, receptors, antibodies, affibodies, antigens, aptamers, haptens, hormones, enzymes, enzyme substrates, or combinations thereof.

The term "plurality of targets," or "plurality of different targets" as used herein, refers to two or more different targets. For example, a plurality of targets in a biological may refer to a plurality of antigens in the biological sample, wherein the plurality of antigens comprise at least two different types of antigens (e.g., a mixture of antigen A and antigen B). In general, the plurality of targets comprises at least two sets of different targets; each set of different targets comprising at least one target. The two sets of different targets may comprise same type of biomarkers (e.g., two sets of different antigens; a first set of antigen A, and a second set of antigen B) or it may comprise different types of biomarkers (e.g., a first set of RNA, and a second set of DNA). Each set of different targets may often comprise more than one target.

The term "target-binding probe," as used herein, refers to a moiety that is capable of specifically binding to a target. The target-binding probe may be used to detect or analyze a target when the target is present in the biological sample. The target-binding probe comprises at least one target-binding moiety. The target-binding moiety may be a naturally occurring specific binder of the target, a moiety that is derived from the naturally occurring specific binder, or a synthetic moiety that specifically binds to the target. For example, a target-binding probe to detect a target antigen may be derived from an antibody that is specific to the target antigen. The target-binding probe may further comprise a signal-generating moiety, a masked signal-generating moiety, a cross-linking moiety, or an independently detectable moiety associated (either covalently or non-covalently) with the target-binding moiety. Often, the target-binding probes bind the target via molecular recognition of discrete chemical moieties of the target or structural components of the target (e.g., via molecular recognition of a specific three-dimensional structure of a protein). Suitable examples of target-binding probes include, but are not limited to, a DNA, a RNA, a locked nucleic acid (LNA), a peptide nucleic acid (PNA), a modified oligonucleotide (e.g., oligonucleotide with a modified base, a modified sugar moiety, or a modified phosphate moiety), an antibody, an antibody fragment, a peptide, an affibody, a hapten, a ligand, or an aptamer.

The term "specific binding," as used herein, refers to the specific recognition of one of two different molecules (partner molecules) for the other compared to substantially less recognition for other, non-partner molecule(s). Generally specificity of a binding event results from specific molecular recognition sites in the partner molecules. The molecules may have recognition sites either on their surfaces or in their cavities that give rise to specific recognition between the two partner molecules. Molecular recognition may result via electrostatic interaction, hydrogen bonding, hydrophobic interaction, or a combination of interactions thereof. Examples for specific binding interactions include, but are not limited to, antibody-antigen interaction, enzyme-substrate interaction, complementary nucleic acid sequence hybridization, ligand-receptor interaction, and the like. Target-binding probes are selected in such a way that they bind specifically to their respective targets.

The terms "signal generator," or "signal-generating moiety" as used herein, refers to a molecule that provides or generates a detectable signal. The signal generator may provide a detectable signal inherently, without requiring any prior chemical or structural modification for generating the detectable signal (e.g., fluorescence signal from a fluorophore), or may generate a detectable signal via interaction with another suitable moiety (e.g., signal generation by an enzyme via enzyme-substrate reaction). The detectable signal may include an optical signal, an electrical signal, an acoustic signal, or a radioactive signal. The detectable signal may be observed using one or more detection techniques such as spectrometry, spectroscopy, or visual inspection. Examples of suitable signal generators include, but are not limited to, a chromophore, a fluorophore, a Raman-active tag, a radioactive label, an enzyme, or a combination thereof.

The term "masked signal-generating moiety," as used herein, refers to a precursor signal generator (pro-signal generator), wherein the detectable signal of the signal generator is masked. The masking may modify at least one of the signal characteristics. Masking may result in complete/partial removal of signal, a shift in signal peak, a reduction in signal intensity, or a shift in signal frequency. The masked signal-generating moiety may be converted to a signal generator upon unmasking. For example, a target-binding probe having a masked signal-generating moiety may comprise an antibody (a target-binding moiety) coupled with a quenched fluorophore (a masked signal-generating moiety). A donor-acceptor fluorophore pair (e.g., a fluorophore-quencher pair) may be used as the masked signal-generating moiety (a masked fluorophore), wherein the fluorescence of the donor is quenched via a resonance energy transfer to the acceptor. Modifying the distance between donor and acceptor, or removal of the acceptor may be used to unmask the donor fluorophore, and the fluorescence from the donor may then be observed.

The term "independently detectable moiety", as used herein refers to a moiety that may be detected either by a direct assay or by an indirect assay. To be detected by the direct assay, the independently detectable moiety should comprise a signal generator (i.e., it should provide/generate a detectable signal). When independently detectable moiety does not produce a detectable signal by itself or when it contains a masked signal-generating moiety, indirect assays need to be employed to detect the independently detectable moiety. For example, the independently detectable moiety may then be detected by associating it with a signal-generating moiety or by un-masking the signal-generating moiety.

The term "correlating", as used herein, refers to comparing or analyzing in any way the performance and/or results to establish a mutual or reciprocal relationship between the events that are being correlated.

The term "in situ," refers to an event occurring in the original or native location. For example, in situ may refer to an event occurring in an intact organ or tissue, or in a representative segment of an organ or tissue. In situ analysis of targets often provides contextual information that may be lost when the target is removed from its site of origin. In situ analysis of targets may be performed on cells, tissues, or tissue sections derived from a variety of sources, including an organism, an organ, a tissue, or a cell culture. Accordingly, in situ analysis of targets in a cell or a tissue describes analysis of target-bound probe located within the whole cell or the tissue sample, wherein target-bound probe remains within the cell. The cell membrane may be fully intact or partially intact while performing the in situ analysis. Furthermore, the methods may be employed to analyze targets in situ in cell or tissue samples that are fixed, unfixed or frozen.

The term "observing a signal" refers to detecting, characterizing, or monitoring the signal. A signal from a signal generator may be observed using a detection system or an imaging system. For example, observing a signal from a biological sample may be preformed by capturing an image of the biological sample. The nature of the detection system or the imaging system used depends upon the nature of the signal that is generated by the signal generator. Non-limiting examples of detection/imaging system that may be used to observe a signal include an electron spin resonance (ESR) system, a charge coupled device (CCD) system (e.g., for radioisotopes), an optical system (e.g., optical imaging, fluorescence imaging, confocal imaging), an electrical system, a photographic film system, a chemiluminescent system, an enzyme detection system, an atomic force microscopy (AFM) system, a scanning tunneling microscopy (STM) detection system, a near infra-red field system, or a total internal reflection (TIR) system. Observing a signal also includes visual observation of a signal.

One or more of the methods may be used in analytical, diagnostic, or prognostic applications such as, but not limited to, analyte detection, disease detection, disease monitoring, treatment monitoring, disease prediction, histochemistry, cytochemistry, immunochemistry, immunohistochemistry, or immunofluorescence. For example, the methods may be particularly useful in the fields of histochemistry, immunohistochemistry, or immunofluorescence.

The methods may be used to detect a plurality of targets in a single biological sample. The detection of the plurality of targets may comprise identifying the presence, absence, location and/or amount of the plurality of targets. The methods may use a single detection channel for detecting the plurality of targets. In some embodiments, the methods may be used for in vitro analysis of biological samples. In some embodiments, the methods may be used for in vivo analysis of biological samples.

The methods enable detection of a plurality of targets in the same biological sample. Detecting the targets in the same biological sample may also be used to determine spatial information about the targets in the biological sample. The methods are useful in analytical applications where a limited amount of biological sample may be available for analysis, or where the same sample must be processed for multiple analyses. The same detection channel may be employed multiple times for detecting different targets in the same sample, enabling fewer chemistry requirements for analyses of multiple targets. The methods are also useful in instances wherein conventional detection methods may be capable of detecting only a limited number of targets due to limitations in resolving overlapping signals. For example, in a conventional fluorescent-based detection assay, the number of targets that may be simultaneously detected may be limited to about four because more than four fluorescent signals may not be resolvable based on their excitation and emission wavelength properties. The methods of the invention may help overcome this limitation, and enable the detection of multiple targets (e.g., greater than the four targets). The method may be used to detect a plurality of targets that may help in comparing different types of cells or tissues, comparing different developmental stages, detecting the presence of a disease or abnormality, or determining the type of a disease or abnormality.

The methods further provides means of increasing mutiplexity of the detection of the targets by using target-binding probes having activatable labels (e.g., signal generators) that can be activated for imaging in conjunction with target-binding probes having labels that are already imageable. This allows for simultaneous use of two or more target-binding/detecting agents, one of which is directly detectable while the others can only be detected after activation, allowing reuse of same detection channel for detection. The methods describe use of activatable labels along side active labels that may be activated after the already active labels have been imaged. It is also possible to employ multiple activatable labels each activatable under same conditions if the labels are detected in different detection channels or under different conditions if the same detection channel is used for detection. The already imageable label may be cleaved off before or at the same time the activatable label is activated using appropriate linker and protective group chemistries. The invention further describes methods of amplifying signal to detect multiple specific molecules that may be present at different concentration. Multiple ways of amplification to achieve different levels of amplification may be used simultaneously. Another feature of the invention is signal amplification in a multiplexed format using multiply labeled oligonucleotides or polymers and/or in situ polymerization.

The biological samples include, but are not limited to, blood, plasma, serum, saliva, cerebral spinal fluid, pleural fluid, milk, lymph, sputum, semen, urine, stool, tear, saliva, needle aspirate, external section of the skin, respiratory, intestinal, or genitourinary tract, tumor, organ, cell culture, cell culture constituent, tissue sample, tissue section, whole cell, cell constituent, cytospin, or cell smear. The biological sample may exist in a solid or a fluid form, and may comprise a frozen, a fixed, a stained, or a pre-treated sample. The biological sample may further include compounds such as preservatives, anticoagulants, buffers, fixatives, nutrients, antibiotics, or the like, which may not naturally intermixed with the sample in its native form. The biological sample may be analyzed as is, i.e., without harvest and/or isolation of the target of interest, or may be subjected to harvesting and/or isolation of targets prior to analysis.

The biological sample may comprise a whole cell. The cell may be a primary cell, a cultured cell, or a cell line. The biological sample may comprise stem cells (e.g., adult stem cells, or embryonic stem cells), dedifferentiated somatic cells, reprogrammed cells, or induced pluripotent cells. The stem cell may be totipotent, pluripotent, or multipotent.

The biological sample may comprise a tissue sample. The tissue sample comprises a collection of similar cells (not necessarily identical cells, but cells from the same origin) obtained from a biological subject that may have a similar function. For example, human tissues include, but are not limited to, epithelial tissues (e.g., surface of skin, airways, reproductive tract, or the inner lining of the digestive tract), connective tissues (e.g., blood vessels, bone, or cartilage), muscle tissues (visceral or smooth muscles, skeletal muscle, or cardiac muscle), or nerve tissues (e.g., brain, cranial nerves, or spinal cord). The tissue sample may be obtained during any time in gestation (prenatal) or development of the biological subject, from a fresh or a preserved (e.g., fixed or frozen) organ, biopsy, aspirate, blood, blood constituents, or bodily fluid (e.g., cerebral spinal fluid, amniotic fluid, peritoneal fluid, or interstitial fluid).

The tissue sample may be a thin slide of a tissue or its part (a tissue section), derived either from a normal tissue (e.g., a tissue section of colon, breast, or prostate) or a diseased tissue (e.g. colon adenocarcinoma). The tissue section may have a thickness in a range of about 1 micrometer (µm) to about 100 µm, or about 1 µm to about 50 µm, or about 2 µm to about 25 micrometers, or about 3 µm to about 5 micrometers. The same section of tissue sample may be taken and subjected to analysis to detect at least two sets of different targets at a morphological level or at a molecular level. In some embodiments, multiple sections of a tissue sample may be analyzed to detect a plurality of targets. The tissue sample may be provided in the form of a tissue micro array (e.g., a breast tissue micro array).

In some embodiments, method of detecting a plurality of targets in a biological sample comprises sequential detection of the plurality of targets in the biological sample. First, a plurality of target-binding probes is simultaneously added to the biological sample to form a plurality of target-bound probes. At least one of the target-bound probes is then covalently attached to the biological sample. The plurality of targets is then detected sequentially by detecting the target-bound probes. One or more of the methods may comprise the steps of contacting the sample with a plurality of target-binding probes to form a plurality of target-bound probes, covalently attaching at least one of the target-bound probes to the biological sample, observing a first set of signals from a first set of the plurality of target-bound probes, modifying the observed signals, generating a second set of signals from a second set of the plurality of target-bound probes, and observing the second set of signals.

The method generally comprises the steps of applying a plurality of multiple sets of target-binding probes to the biological sample, covalently attaching at least one of the target-bound probes to the biological sample, detecting a first set of the plurality of targets in the biological sample by observing a first set of signals from the first set of plurality of targets, modifying the observed first set of signals, and detecting a second set of the plurality of targets in the biological sample (via generating a second set of signals from the second set of plurality of targets and observing the second set of signals). The method may further comprise repeating the step of modification of the observed signal from the second set of the plurality of targets (i.e., second set of signals) followed by detecting a third set of the plurality of targets in the biological sample. The above method steps may be repeated multiple times (to detect a fourth, a fifth, and an $n^{th}$ set of the plurality of targets) to detect most or all of the plurality of targets in the biological sample. In some embodiments, the steps are repeated about 100 times to detect about 100 different sets (i.e., n=100) of targets. The first set of signals and the subsequent set of signals may all be of the same type (e.g., a fluorescent signal) or they may be of different types (e.g., first set may be a fluorescent signal and second set may be an absorption signal). The first set of signal and the subsequent set of signals may use a single detection channel or may employ multiple detection channels.

In some embodiments, the plurality of targets in the biological sample comprises at least two sets of different targets; each set of different targets comprising at least one target. The two sets of different targets may comprise same type of biomarkers (e.g., two sets of different antigens, a first set of antigen A and a second set of antigen B) or it may comprise different types of biomarkers (e.g., a first set of antigen A and a second set of DNA). In some embodiments the plurality of targets may comprise multiple sets of different targets. The target may be present on the surface of the biological sample (e.g., on the surface of histological sections, DNA microarrays, protein microarrays, cells in suspension, cytology smears, or solid supports (such as gels, blots, glass slides, beads, or ELISA plates), or may be buried inside (e.g., RNA or DNA targets in a cell for in situ detection). The targets may be characteristic of a particular cell type (e.g., differentiated versus un-differentiated stem cells), or a particular disease or medical condition. Suitable targets include, but are not limited to, peptides, proteins, oligonucleotides, nucleic acids (e.g., deoxyribonucleic acids (DNA), or ribonucleic acids (RNA)) polysaccharides (e.g., lectins or sugars), lipids, ligands, receptors, antibodies, affibodies, antigens, aptamers, haptens, lipids, hormones, enzymes, enzyme substrates, or combinations thereof.

The methods may be used to detect a plurality of different targets, including, but not limited to, prognostic targets, hormone or hormone receptor targets, lymphoid targets, tumor tissue targets, cell cycle-associated targets, neural tissue targets, or cluster of differentiation (CD) targets, or combinations thereof. Non-limiting examples of targets include, centromere protein-F (CENP-F), giantin, involucrin, lamin A&C (XB 10), LAP-70, mucin, nuclear pore complex proteins, p180 lamellar body protein, ran, cathepsin D, Ps2 protein, Her2-neu, P53, S100, epithelial target antigen (EMA), TdT, MB2, MB3, PCNA, or Ki67.

Non-limiting examples of tumor tissue targets may include biomarkers such as breast cancer biomarkers (e.g., ER, PR, Her2, CA 15-3, CA 27.29, CEA, uPA, PAI-1, or Ki-67), colorectal cancer biomarkers (e.g., CEA, CA19-9, Thymidylate Synthase, or CA125), lung cancer biomarkers (e.g., NSE, CEA, CYFRA 21-1, IMP3, TPA, proGRP, TTF, D2-40, Podoplanin, Cytokeratin-20, Chromogranin A, or Serum Amyloid A), prostate cancer biomarkers (e.g., PSA, PCA3, uPM3, hk2, or PSMA), or liver cancer biomarkers (e.g., AFP).

Suitable examples of prognostic targets may include, but are not limited to, enzymatic targets such as galactosyl transferase II, neuron specific enolase, proton ATPase-2, or acid phosphatase. Hormone, hormone-regulating, or hormone-receptor targets may include, but are not limited to, human chorionic gonadotropin (HCG), adrenocorticotropic hormone, carcinoembryonic antigen (CEA), prostate-specific antigen (PSA), estrogen receptor, progesterone receptor, androgen receptor, gC1q-R/p33 complement receptor, IL-2 receptor, p75 neurotrophin receptor, PTH receptor, thyroid hormone receptor, or insulin receptor.

Suitable examples of lymphoid targets may include, but are not limited to, alpha-1-antichymotrypsin, alpha-1-antitrypsin, B cell target, bcl-2, bcl-6, B lymphocyte antigen 36 kD, BM1 (myeloid target), BM2 (myeloid target), galectin-3, granzyme B, HLA class I Antigen, HLA class II (DP) antigen, HLA class II (DQ) antigen, HLA class II (DR) antigen, human neutrophil defensins, immunoglobulin A, immunoglobulin D, immunoglobulin G, immunoglobulin M, kappa light chain, kappa light chain, lambda light chain, lymphocyte/histocyte antigen, macrophage target, muramidase (lysozyme), p80 anaplastic lymphoma kinase, plasma cell target, secretory leukocyte protease inhibitor, T cell antigen receptor (JOVI 1), T cell antigen receptor (JOVI 3), terminal deoxynucleotidyl transferase, or unclustered B cell target.

The tumor tissue targets may include, but are not limited to, alpha fetoprotein, apolipoprotein D, BAG-1 (RAP46 protein), CA19-9 (sialyl lewisa), CA50 (carcinoma associated mucin antigen), CA125 (ovarian cancer antigen), CA242 (tumor associated mucin antigen), chromogranin A, clusterin (apolipoprotein J), epithelial membrane antigen, epithelial-related antigen, epithelial specific antigen, gross cystic disease fluid protein-15, hepatocyte specific antigen, heregulin, human gastric mucin, human milk fat globule, MAGE-1, matrix metalloproteinases, melan A, melanoma target (HMB45), mesothelin, metallothionein, microphthalmia transcription factor (MITF), Muc-1 core glycoprotein, Muc-1 glycoprotein, Muc-2 glycoprotein, Muc-5AC glycoprotein, Muc-6 glycoprotein, myeloperoxidase, Myf-3 (Rhabdomyosarcoma target), Myf-4 (Rhabdomyosarcoma target), MyoD1 (Rhabdomyosarcoma target), myoglobin, nm23 protein, placental alkaline phosphatase, prealbumin, prostate specific antigen, prostatic acid phosphatase, prostatic inhibin peptide, PTEN, renal cell carcinoma target, small intestinal mucinous antigen, tetranectin, thyroid transcription factor-1, tissue inhibitor of matrix metalloproteinase 1, tissue inhibitor of matrix metalloproteinase 2, tyrosinase, tyrosinase-related protein-1, villin, or von Willebrand factor.

Non-limiting examples of cell cycle-associated targets include, apoptosis protease activating factor-1, bcl-w, bcl-x, bromodeoxyuridine, cdk-activating kinase (CAK), cellular apoptosis susceptibility protein (CAS), caspase 2, caspase 8, CPP32 (caspase-3), CPP32 (caspase-3), cyclin dependent kinases, cyclin A, cyclin B1, cyclin D1, cyclin D2, cyclin D3, cyclin E, cyclin G, DNA fragmentation factor (N-terminus), Fas (CD95), Fas-associated death domain protein, Fas ligand, Fen-1, IPO-38, Mcl-1, minichromosome maintenance proteins, mismatch repair protein (MSH2), poly (ADP-Ribose) polymerase, proliferating cell nuclear antigen, p16 protein, p27 protein, p34cdc2, p57 protein (Kip2), p105 protein, Stat 1 alpha, topoisomerase I, topoisomerase II alpha, topoisomerase III alpha, or topoisomerase II beta.

The neural tissue targets may include, but are not limited to, alpha B crystallin, alpha-internexin, alpha synuclein, amyloid precursor protein, beta amyloid, calbindin, choline acetyltransferase, excitatory amino acid transporter 1, GAP43, glial fibrillary acidic protein, glutamate receptor 2, myelin basic protein, nerve growth factor receptor (gp75), neuroblastoma target, neurofilament 68 kD, neurofilament 160 kD, neurofilament 200 kD, neuron specific enolase, nicotinic acetylcholine receptor alpha4, nicotinic acetylcholine receptor beta2, peripherin, protein gene product 9, S-100 protein, serotonin, SNAP-25, synapsin I, synaptophysin, tau, tryptophan hydroxylase, tyrosine hydroxylase, or ubiquitin.

Suitable examples of cluster differentiation targets include, but are not limited to, CD1a, CD1b, CD1c, CD1d, CD1e, CD2, CD3delta, CD3epsilon, CD3gamma, CD4, CD5, CD6, CD7, CD8alpha, CD8beta, CD9, CD10, CD11a, CD11b, CD11c, CDw12, CD13, CD14, CD15, CD15s, CD16a, CD16b, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42a, CD42b, CD42c, CD42d, CD43, CD44, CD44R, CD45, CD46, CD47, CD48, CD49a, CD49b, CD49c, CD49d, CD49e, CD49f, CD50, CD51, CD52, CD53, CD54, CD55, CD56, CD57, CD58, CD59, CDw60, CD61, CD62E, CD62L, CD62P, CD63, CD64, CD65, CD65s, CD66a, CD66b, CD66c, CD66d, CD66e, CD66f, CD68, CD69, CD70, CD71, CD72, CD73, CD74, CDw75, CDw76, CD77, CD79a, CD79b, CD80, CD81, CD82, CD83, CD84, CD85, CD86, CD87, CD88, CD89, CD90, CD91, CDw92, CDw93, CD94, CD95, CD96, CD97, CD98, CD99, CD100, CD101, CD102, CD103, CD104, CD105, CD106, CD107a, CD107b, CDw108, CD109, CD114, CD115, CD116, CD117, CDw119, CD120a, CD120b, CD121a, CDw121b, CD122, CD123, CD124, CDw125, CD126, CD127, CDw128a, CDw128b, CD130, CDw131, CD132, CD134, CD135, CDw136, CDw137, CD138, CD139, CD140a, CD140b, CD141, CD142, CD143, CD144, CDw145, CD146, CD147, CD148, CDw149, CDw150, CD151, CD152, CD153, CD154, CD155, CD156, CD157, CD158a, CD158b, CD161, CD162, CD163, CD164, CD165, CD166, or TCR-zeta.

The plurality of targets in a biological sample is detected by employing a plurality of probes that are capable of binding the targets (target-binding probes) via a target-binding moiety. The plurality of target-binding probes comprises multiple sets of probes, wherein each set of probe may be structurally or functionally different from another set. The target-binding probes are bound to the targets by contacting and subsequently incubating the target-binding probes with the biological sample. Prior processing of the biological sample may be required (e.g., antigen retrieval) to make the targets accessible for the binding of target-binding probes. When the target-binding probe is bound to the target, the detection of the target may be achieved by detecting the target-bound probe. The target-binding probes may or may not comprise a signal generator. When the target-binding probe comprises a signal generator, the detection of the target may be achieved by observing a signal from the signal generator. When a target-binding probe does not comprise a signal generator, a signal-generating moiety that binds specifically to the target-bound probes may be associated with the target-bound probe to enable the detection of the targets.

In some embodiments, the target-binding probe comprises a unit derived from a target-binding moiety and an independently detectable moiety. The independently detectable moiety may be a signal generator such as a fluorophore, chromophore, a Raman tag, a Surface Enhanced Raman Spectroscopy (SERS) tag, a Surface Enhanced Resonance Raman Spectroscopy (SERRS) tag, or a radioisotope. In some embodiments, the independently detectable moiety comprises a moiety that may be detected using an indirect assay. For example, the independently detectable moiety may be a unique nucleic acid sequence, a hapten, an enzyme, or a combination thereof. In some embodiments, the independently detectable moiety comprises a masked signal-generating moiety. Examples of a masked signal-generating moiety includes, but are not limited to, a masked fluorophore, a masked chromophore, a masked Raman tag, a masked SERS tag, a masked SERRS tag, or a combination thereof. A masked fluorophore may comprise a donor-acceptor fluorophore pair (e.g., fluorescein-rhodamine pair), a quenched fluorophore (e.g., quenched by a metal or by an organic moiety), or a polarity-sensitive fluorophore (e.g., Prodan; 6-propionyl-2-dimethylaminonaphthalene, Paldan; 6-palmitoyl-2-dimethylaminonaphthalene, or Laurdan; 6-dodecanoyl-2-dimethylaminonaphthalene).

Independently detectable moiety may be attached to the target-binding moiety via covalent bonding (either by direct attachment without a linker moiety or by attachment through a linker moiety) or non-covalent interaction (e.g., electrostatic interaction, van der Waals interaction, dipole-dipole interactions, hydrogen bonding, or a combination thereof). In some embodiments, the independently detectable moiety is attached to the target-binding moiety via a cleavable linker. Cleavable linker may comprise a cleavable covalent bond (e.g., S—S bond) that may be cleaved (e.g., by oxidation, nucleophilic substitution, reduction, or pH change) or comprise a binding pair (e.g., complementary nucleic acids, or dethioavidin-biotin pair), which may be dissociated under suitable conditions.

In some embodiments, the target-binding probe comprises a target-binding moiety, a cross-linking moiety, and an independently detectable moiety. For example, the target-binding probe for a RNA target may comprise three regions, a first region comprising an oligonucleotide that is complementary to the target RNA (i.e., the target-binding moiety), a second region comprising an oligonucleotide (i.e., the independently detectable moiety, a zip code) that may be complementary to a labeled oligonucleotide probe (i.e., a signal generator), and a third region comprising an oligonucleotide having a cross-linking moiety, which is capable of cross-linking the target-binding probe to a molecule that is located in the vicinity of the target RNA. The cross-linking moiety may be attached to the oligonucleotide in the third region via a linker moiety. The cross-linking of the target-binding probe may be initiated by exposing the target-binding probe to a suitable initiating agent (e.g., light or a chemical agent). The target-binding moiety, the cross-linking moiety and the independently detectable moiety may be positioned in the target-binding probe in any order. For example, in some embodiments, the target-binding moiety may be directly attached to both the cross-linking moiety and the independently detectable moiety. In other example, the target-binding moiety may be directly attached to the cross-linking moiety, and the cross-linking moiety may in turn be directly attached to the independently detectable moiety. In another example, the target-binding moiety may be directly attached to the independently detectable moiety, and the independently detectable moiety may in turn be directly attached to the cross-linking moiety.

The target-bound probes may be detected either directly or indirectly depending on the nature of the independently detectable moiety. For example, when the independently detectable moiety provides a detectable signal (e.g., an optical signal or a radioactive signal) by itself, a direct detection method may be employed. When the independently detectable moiety does not provide a detectable signal by itself, a prior signal generation step may be needed to detect the target-bound probe (indirect detection). For example, when the independently detectable moiety is a nucleic acid sequence, it may be hybridized with a labeled, complementary nucleic acid sequence, and the hybridization complex may then be detected by observing the signal from the label.

In some embodiments, the plurality of targets in the biological sample is detected by simultaneous application of target-binding probes, followed by sequential detection of the target-bound probes. The plurality of targets comprises at least two sets of different targets, wherein each set of different targets comprises at least one target. The plurality of target-bound probes comprise at least two sets of different target-bound probes; each set of different target-bound probes comprising at least one target-bound probe. In one example, the method comprises the steps of contacting a biological sample with a plurality of target-binding probes to form a plurality of target-bound probes. At least one of the target-bound probes is then covalently attached to the biological sample. The plurality of different sets of target-bound probes is then detected in a sequential manner. In general, the different sets of target-bound probes are sequentially detected one set at a time. At first, a first set of signals may be observed from a first set of the plurality of target-bound probes. This first set of signals may comprise signals that are indistinguishable from each other, or they may comprise signals that are distinguishable from each other on the basis of spectral differences or type of signal. The observed signals are then modified. The signals may be modified by using any of the signal modifying procedures, such as, bleaching (e.g., photo bleaching or chemical bleaching). A second set of signals may then be generated from a second set of the plurality of target-bound probes followed by observing the second set of signals. The method may further include the steps of modifying the observed signals (i.e., the second set of signals), generating a third set of signals from the plurality of target-bound probes followed by observing the third set of signals. The steps of "modifying the observed signals", and "generating followed by observing" a subsequent set of signals may be repeated multiple times with a fourth, a fifth and an $n^{th}$ set of the plurality of target-bound probes to observe a fourth, fifth, and an $n^{th}$ set of signals. Potentially an infinite number of targets (i.e., here, the integer value of n may range from n=6 to n=∞) may be sequentially detected by employing this method. During the modification of observed signals, it may be not necessary to modify all the observed signals. One or more of the observed signals may be preserved without modification. The one or more of the preserved signals may be then utilized for co-registration or comparative analysis. The method may further comprise steps of correlating the observed signals to the detection of the plurality of targets in the biological sample.

If multiple sets of target-bound probes produce mutually distinguishable signals that can be resolved (e.g., on the basis of spectral differences or type of signals) from one another, the method may be modified to sequentially detect batches of multiple sets of target-bound probes. For example, a sequential detection of target-bound probes that generate fluorescent signals may be performed by detecting a first batch of 4 sets of different target-bound probes (e.g., by using a 4-channel detection) at a time if fluorescence from each of the 4 sets of different target-bound probes is resolvable from one another. Once signals from the first batch of 4 sets of different target-bound probes are observed, the observed signals are modified. Following this, a second batch of 4 sets of different target-bound probes may be detected by generating signals from the second batch and observing the generated signals. In general, the number of sets of different target-bound probes that can be detected at a time in each batch depends on the capability of the device, which is used to observe the signals, to resolve the signals of each set from one another. The signals may be resolvable from each other due to non-overlapping spectral characteristics, due type of signals (e.g., fluorescent signal and radioactive signal), or due to different localization in the biological sample (e.g., signal from cytoplasm and signal from nucleus). The steps may be repeated till all the different target-bound probes are sequentially detected.

In some embodiments, after contacting the target-binding probes with the biological sample, the biological sample may be incubated for a time period that is sufficient for specific binding of the target-binding probes to the targets. The incubation may be performed at room temperature for a time span of about 5 minutes to about 16 hours, or at 4° C. for about 16 hour. The incubation temperature and the time span of incubation depend primarily on the functional and/or structural characteristics (e.g., melting temperature ($T_m$) of an oligonucleotide probe) of the target-binding probe used. The target-binding moiety may be bound to the target via non-covalent interactions, including, but are not limited to, electrostatic interaction, van der Waals interaction, dipole-dipole interactions, or hydrogen bonding. The method may, optionally, comprise further steps for removing any target-binding probes that may not have bound to the targets. Removal of any un-bound probes may be achieved by washing the biological sample with a suitable buffer.

The plurality of target-binding probes may comprise one or more target-binding probes that are capable of covalently binding to the biological sample. In some examples, all of the plurality of target-binding probes may be capable of covalently binding to the biological sample. The covalent attachment of the target-binding probes to the biological sample may be via the target itself or via a molecule that is located in the vicinity of the targets. Generally, the plurality of target-binding probes are contacted with the biological sample and incubated. Often the plurality of target-binding probes first gets bound to the target via physical interactions (i.e., non-covalent interactions such as hydrogen bonding, Van der Waals interactions and the like) to generate the plurality of target-bound probes. Under suitable conditions, one or more of the plurality of target-bound probes may then be covalently coupled to the target itself or to a molecule that is located in the vicinity of the target. In some cases, all of the plurality of target-bound probes may be covalently coupled/cross-linked to the biological sample. The covalent attachment of the target-binding probes to the target or to a molecule that is located in the vicinity of the target may be achieved by direct coupling (e.g., cross-linking of proteins or nucleic acids) or via a linker moiety (e.g., via a bi-functional linker moiety). When the covalent attachment is performed via a linker moiety, linker lengths are selected such that they are insignificant (e.g., about 5 Å to about 50 Å) when compared to the dimensions of a biological cell. Thus, even if the target-binding probes are getting cross-linked to a molecule that is located in the vicinity of the target, the location of the bound probe may be practically the same as that of the target. The covalent coupling may comprise a covalent link that is irreversible (e.g., a C—C bond), a bond that is reversible (e.g., formation of an S—S bond) or a bond that is cleavable (e.g., coupling via a cleavable linker). The covalent coupling may be achieved by photo cross-linking or by chemical cross-linking via an ester, an amide or a thioether bond formation. The covalent coupling of the target-binding probe to the target may help to retain the signature of the targets while performing the subsequent methods steps for detecting the plurality of targets. The term signature means that although the target may be destroyed in subsequent manipulations, its presence in the sample can be inferred from the presence of the target-bound probe, which initially selectively bound to the target and was cross-linked in place. Covalent attachment of the target-binding probe to the target is particularly relevant when the targets may be susceptible to various agents that are being used for the signal generation and signal modification. For example, RNA targets may be susceptible to a chemical agent that may be used for modifying the observed signal. So, while detecting a plurality of different RNA targets by observing signals from a plurality of RNA-bound probes, there exists a possibility of destroying a subsequent set of RNA targets while generating a signal or modifying the observed signal from a first and/or a second set of RNA targets. However, if the RNA-binding probes are cross-linked to the target RNA or to a molecule in the vicinity of the target RNA, even if the RNA target is destroyed in subsequent manipulations, its presence in the sample can be inferred from the presence of the bound probe (either bound to the target RNA or bound to the biological sample), which initially selectively bound to the RNA target and was cross-linked in place. In fact, in some example it might be beneficial to destroy all the cellular RNA by treating the biological sample with RNAse once the target-bound probes are cross-linked to a biological sample. Moreover, more stringent washing conditions may be used to remove any unbound target-binding probes if the target-binding probes are cross-linked to the biological sample. This procedure increases the signal-to-noise ratio while detecting a plurality of RNA targets in a biological sample.

The first set of signals from the first set of the plurality of target-bound probes may be observed either directly or indirectly. When a direct assay is employed, the first set of the plurality of target-binding probes (i.e., the set of probes that bind to the first set of the plurality of targets to form the first set of target-bound probes) comprises a unit derived from a target-binding moiety and an independently detectable moiety, wherein the independently detectable moiety is capable of producing an observable signal by itself (i.e., the independently detectable moiety comprises a signal generator).

In some embodiments, the first set of target-binding probes may comprise a target-binding moiety (e.g., antibodies, nucleic acids, aptamers, affibodies, or haptens) that is labeled with a signal generator (e.g., a fluorophore, a chromophore, a radioisotope, an enzyme, or a Raman active moiety). The signal generator produces an observable signal that can be detected or visualized directly. For example, when the first set of target binding probes consists of probes having a fluorophore attached to a target-binding moiety, upon binding to the targets, the target-bound probes may be detected by observing a fluorescence signal from the fluorophore. The signal generator may produce an observable signal either inherently (e.g., a fluorogenic signal generator) or by interaction with a suitable substrate (e.g., an enzyme-substrate reaction for an enzymatic signal generator).

Indirect detection of the first set of target-bound probes is employed when a first set of target-binding probes do not provide an observable signal by itself. In some embodiments, this may be achieved by associating a signal-generating moiety with the first set of target-bound probes. For example, the first set of target binding probes may comprise un-labeled primary probes (e.g., primary antibodies), which may be used to bind a first set of targets (e.g., antigens) in a biological sample. Labeled, secondary probes (e.g., labeled, secondary antibodies) may be then used to tag the target-bound primary probes. The tagged, target-bound primary probes may be then detected by observing a signal from the labeled, secondary probes (which are bound to the primary probes). The detection of the tagged primary probe may then be correlated to the presence of the first set of targets in the biological sample. Indirect assays may be effectively used to increase the sensitivity of detection since the primary probe may be tagged with several secondary probes, subsequently enhancing the signal-to-noise ratio.

After observing the first set of signals from the first set of target bound probes, either directly or indirectly, the observed signals are modified. Signal modification may include a change in at least one signal characteristic. For example, the signal modification may include, but is not limited to, a decrease in intensity of signal, a shift in signal peak, a change in resonant frequency, or removing the signal (signal destruction). The modification of the observed signal helps avoiding overlapping of signals (already observed signals v. signals to be observed) during the detection of subsequent sets of the target-bound probes.

Any signal modification methods such as bleaching (e.g., photo-bleaching, or chemical bleaching), quenching (e.g., metal ions for quenching fluorescence), or sequestering (e.g., by using chelators) may be used to modify an observed signal. In some embodiments, a chemical agent is applied to modify the observed signal. Suitable chemical agents useful to modify the observed signal include, but are not limited to, agents that modify pH (e.g., acids or bases), nucleophiles, electrophiles, oxidizing agents, reducing agents, or a combination thereof. For example, a 3% $H_2O_2$ in 200 mM $NaHCO_3$ at basic pH may be used to modify the fluorescence of a cyanine (e.g., Cy3 or Cy5) dye.

After observing and subsequently modifying the first set of signals from the first set of the target-bound probes, signals from a second and a subsequent set of target-bound probes may be observed. The second and subsequent sets of the target-bound probes are detected via indirect assays since the second and subsequent sets of target-binding probes are selected such that they do not produce an observable signal inherently. So, a prior signal generation step is required for generating the signals from the second and subsequent sets of targets bound probes. This may be achieved by associating a signal-generating moiety to the second or subsequent sets of target-bound probes, and observing the signal from the signal-generating moiety.

In some embodiments, the second and subsequent sets of target-binding probes comprise a unit derived from a target-binding moiety and an independently detectable moiety, wherein the independently detectable moiety does not produce an observable signal by itself. For example, the independently detectable moiety may comprise a unique nucleic acid sequence, a hapten, an enzyme, or a combination thereof. The target-bound probes may be indirectly assayed by associating a signal-generating moiety (e.g., a label) to the independently detectable moiety. For example, a target-bound probe having a hapten as an independently detectable moiety may be detected by binding a labeled, anti-hapten to the target-bound probe (via hapten-anti-hapten interaction), and then observing a signal from the label.

In some embodiments, the simultaneous application followed by sequential detection of target-binding probes may be used to detect two sets of targets. However, the methods may be used iteratively to detect more than two sets of targets in the same biological sample (e.g., a same tissue section). The upper limit of the number of targets (i.e., sets of different targets) that could be detected often depends on the type of biological sample used, and on the chemistry used for signal generation and signal modification. Harsher methods may affect the integrity of the biological sample once the method steps are repeated a couple of times. However, by selecting suitable, mild (less harsh) conditions, the method steps may be used effectively to detect a large number of targets (e.g., 10 to 100 sets of targets), without compromising the integrity of the biological sample.

The observed signals may be correlated to the detection of the plurality of targets. In some embodiments, at least one of the observing or correlating steps may be performed using computer-aided means. Correlation may be performed manually (e.g., visual correlation), semi-automated (e.g., using a correlation algorithm with some user intervention), or may be completely automated (e.g., using a correlating algorithm in a computer readable media via a computer/robot without any user intervention). In embodiments where the signal(s) are observed and stored in the form of digital image(s), computer-aided analysis of the image(s) may be conducted. Images (e.g., signals from the target-binding probe(s) and morphological stains) may be overlaid using computer-aided superimposition to obtain complete information (e.g., topological and/or correlation information) of the biological sample.

The observed signals (e.g., first, second, or a subsequent set of signals and/or their combinations) may be analyzed to obtain a variety of information regarding the biological sample. For example, a presence or absence of a first set of signal(s) may indicate the presence or absence of the first set of target(s) (capable of binding to the first set of target-binding probes) in the biological sample. Similarly, the presence or absence of a second set signal(s) may indicate the presence or absence of the second set of target(s) (capable of binding to the second set of target-binding probes) in the biological sample. For uses where multiple targets may be analyzed using a plurality of target-binding probes, the presence or absence of a particular signal for a particular set of the target-binding probes may indicate the presence or absence of corresponding target(s) in the biological sample.

In some embodiments, an intensity value of a signal (for example, fluorescence intensity) may be observed, measured, and may be correlated to the amount of target in the biological sample. A correlation between the amount of target and the signal intensity may be determined using calibration standards. In some embodiments, intensity values of the first and second signals may be measured and correlated to the respective target amounts. By comparing the two signal intensities, the relative amounts of the first target and the second target (with respect to each other or with respect to a control) may also be ascertained. Similarly, where multiple targets are analyzed using a plurality of target-binding probes, relative amounts of different targets in the biological sample may be determined by measuring and correlating the different intensities of signals from each of the plurality of target-binding probes.

In some embodiments, one or more control sample may be used, and, by observing a presence or absence of a signal in the biological samples in relation to the control sample (i.e., biological sample of interest versus a control), specific information regarding the biological sample may be obtained. For example, by comparing a diseased tissue sample versus a normal tissue sample, information regarding the targets present/absent only in the diseased tissue sample may be obtained. Similarly by comparing signal intensities between the sample of interest and at least one control, information regarding the differential expression of targets in the sample of interest may be obtained.

In some embodiments, a location of the signal, or relative locations of two or more signals in the biological sample may be observed, for example, using morphological stains or compartmental stains. The location of the signal may be correlated to a location of the target in the biological sample, providing information regarding localization of plurality of different targets in the biological sample. An intensity value of the signal and a location of the signal may be correlated to obtain information regarding localization and concentration of different targets in the biological sample. For example, certain targets may be expressed more in the cytoplasm relative to the nucleus, or vice versa. Information regarding relative localization and amounts of targets may be obtained by comparing location and intensity values of two or more signals.

In some embodiments, the biological sample may be observed (e.g., imaged) prior to contacting the sample with a plurality of target-binding probes to obtain information regarding background signal signature. The background signal signature may be subtracted from the signals observed from the target bound-probes (e.g., first, second, and/or $n^{th}$ target-bound probes) before correlating the observed signals to the detection of targets. The method may further comprise the steps of observing the biological sample after at least one signal modification step to obtain information regarding any residual signal signature. The biological sample may be observed after each signal modification step. The residual signal signature may be used to characterize the signal modification efficiency (e.g., bleaching efficiency), fine-tune the signal modification step such as choice of signal modification agents, time of incubation and/or temperature of incubation. The residual signal signature may also be used to normalize the observed signals from subsequent target-bound probes. The residual signal signature may be subtracted from the observed signals from subsequent target-bound probes prior to correlating the observed signals to the detection of the targets.

In some embodiments, a plurality of targets in a biological sample may be detected by using a plurality of target-binding probes, wherein all the plurality of target-binding probes may be detected by in-direct assays. In one example, the method comprises the steps of contacting the sample with a plurality of target-binding probes to form a plurality of target-bound probes, generating a first set of signals from a first set of the plurality of target-bound probes, observing the first set of signals, modifying the observed signals, generating a second set of signals from a second set of the plurality of target-bound probes, observing the second set of signals, and correlating the observed signals to the detection of the plurality of targets. The method may further comprise the steps of modifying the observed signals and generating a new set of signals multiple times with a third, a fourth, and an $n^{th}$ set of the plurality of target-bound probes, and observing the generated third, fourth, and $n^{th}$ set of signals. The target-binding probes in the above-described methods are not capable of producing a signal by itself. Hence, once the target-binding probes are bound to the targets, a prior signal generation step is required before signals from the target-bound probes are observed.

In some embodiments, the signals are observed by imaging the biological sample. The biological sample may be imaged prior to contacting the sample with the plurality of target-binding probes or prior to the generation of first set of signals from the first set of the plurality of target-bound probes to obtain a background signal signature. In some embodiments, the method may comprise signal-processing steps. For example, the background signal signature may be subtracted from the signals observed in subsequent signal observing steps. The signal-processing steps may be performed prior to, or during the correlation of the observed signals to the detection of the plurality of targets.

In some embodiments, a plurality of nucleic acid targets may be detected in the biological sample. The plurality of nucleic acid targets may comprise at least two sets (a first set and a second set) of different targets. The plurality of targets may comprise, two sets of DNA targets, two sets of RNA targets, or a set of DNA targets and a set of RNA targets. In some embodiments, set of targets may comprise a mixture of at least two different targets (e.g., a mixture of two types of DNA, a mixture of two types of RNA, or a mixture of DNA targets and RNA targets).

When contacted with a plurality of target-binding probes, a first set of targets bind to a first set of probes, wherein the first set of probes are capable of generating a first set of signals under a first set of conditions. For example, RNA targets in a biological sample may be contacted with a plurality of probes comprising a first set of RNA-binding probes (which bind a first set of RNA targets) to generate a first set of RNA target-bound probes. This entire first set of RNA-bound probes may be capable of generating a first set of signals under a first set of conditions. The method may further comprise steps of removing any target-binding probes that are not bound to the targets prior to generating signals from the target-bound probes. In some embodiments, one or more of the target-bound probes may be covalently attached to the biological sample via covalent coupling to the targets itself or to a molecule or a structure that is located in the vicinity of the target. In such instances, the removal of any target-binding probes that are not bound to the targets may be performed prior to covalently attaching the target-bound probes to the biological sample. The first set of RNA-binding probes may be a nucleic acid (e.g., DNA, RNA, LNA or PNA) probe, comprising a target-binding moiety and an independently detectable moiety. For example, the target-binding probe may be a DNA probe comprising a sequence that is complementary to at least one portion of the target RNA sequence (in the first set of targets) and a unique sequence that may be independently detected in an indirect assay. The DNA probes may be incubated with the biological sample under suitable hybridization conditions for a time period that is sufficient for selective hybridization of the DNA probe sequence to the complementary target RNA sequence. The method may further comprise a step of cross-linking the hybridized DNA probe to the target RNA sequence or to a molecule/structure that is located in the vicinity of the target RNA sequence. The target-bound probe may be detected by analyzing the unique sequence. For example, a labeled nucleic acid sequence (e.g., DNA, RNA, PNA or LNA) having sufficient sequence complementary to the unique sequence may be used to tag the target-bound probe. The tagging may be performed by incubating the biological sample with the labeled, complementary nucleic acid sequence under hybridization conditions for a time period that is sufficient for sequence hybridization. The label may include, but are not limited to, chromophore, fluorophore, nanoparticles, Raman active moieties, SERS active moieties or SERRS active moieties, and the like. The target-bound probe may then be detecting by observing (e.g., imaging) the signal from the label. The unique nucleic acid sequence may also be analyzed by indirect assays that include signal amplification procedures (e.g., hybridizing with a nanoparticle comprising a large number of independently detectable moieties (e.g., nucleic acid sequences), and generating a signal from each of the independently detectable moieties).

Another example of the method for detecting a plurality of targets in a biological sample, comprises the steps of; contacting the sample with a plurality of target-binding probes to form a plurality of target-bound probes, covalently attaching at least one of the target-bound probes to the biological sample, contacting the target-bound probes with a first set of signal-generating probes that are capable of binding a first set of the plurality of target-bound probes, and are capable of generating a first set of signals, detecting the first set of the plurality of targets via observing the first set of signals, modifying the observed first set of signals, and repeating the steps of generating signals and modifying observed signals multiple times using a subsequent set of signal-generating probes to detect a subsequent set of the plurality of targets. A chemical agent may be applied to modify the observed signals. The subsequent set of signal-generating probes are capable of binding a subsequent set of the plurality of target-bound probes, and are capable of generating a subsequent set of signals. In some embodiments, the steps may be repeated 10 times, 25 times, 50 times, or 100 times to detects 10 sets of targets, 25 sets of targets, 50 sets of targets, or 100 sets of targets.

The plurality of targets may comprise a DNA, a RNA, a protein, or a combination thereof. In some embodiments, the plurality of targets comprises a plurality of different RNAs. Non-limiting examples of target RNAs that could be detected include, a ribosomal RNA (rRNA), a messenger RNA (mRNA), a transfer RNA (tRNA), a small interfering RNA (siRNA), a transfer messenger RNA (tm RNA), a piwi-interacting RNA (piRNA), a non coding RNA, a regulatory RNA, a CRISPR RNA, a small nuclear RNA (sn-RNA), a small nucleolar RNA (snoRNA), a RNAse-P-RNA, a PUT RNA, a ribozyme, or a micro RNA (miRNA). In some embodiments, the plurality of targets is detected in situ. The methods may be used, for example, to detect transcription initiation sites, or differential gene regulation by in situ imaging of nascent RNA transcripts.

The aforementioned methods for detecting a plurality of targets in the biological samples may be employed to detect multiple batches of the plurality of targets, wherein each batch of the plurality of targets comprises multiple sets of plurality of targets. For example, a plurality of nucleic acids (multiple sets of different nucleic acids) and a plurality of proteins (multiple sets of different proteins) in a biological sample may constitute the two batches of the plurality of targets. First, the plurality of nucleic acids (e.g., two sets of different nucleic acids such as a first set of DNA and a second set of RNA) in the biological sample may be detected by simultaneous application of target-binding probes followed by sequential detection of target-bound probes. The detection of the plurality of proteins (e.g., detection of a first set of protein A and a second set of protein B) may then be performed. For example, a plurality of nucleic acid-binding probes (i.e., DNA-binding probes and RNA-binding probes) may be applied to the biological sample to form a plurality of target nucleic acid-bound probes (a first set of DNA-bound probes and a second set of RNA-bound probes). The signal(s) from the first set DNA-bound probes may then be detected (either by direct assay or an indirect assay depending on if the DNA-bound probes generates a signal by itself or not). The observed signal may then be modified, followed by generation of a second set of signals from the plurality of RNA-bound probes (The signals need to be generated from the second set of target-bound probes since the target-binding probes that hybridize to the second set of nucleic acids are selected such that they do not produce a detectable signal by itself). The generated signals from the RNA-bound probes may then be observed. Once the detection plurality of multiple sets of nucleic acid targets are performed, the method may be used to detect the plurality of multiple sets of proteins. Plurality of target-binding probes that are capable of binding to the target protein A and B (e.g., antibody A and antibody B) may be applied. The antibody A that is bound to protein A may then be detected (first set of proteins) via a direct or indirect assay by observing signals from antibody A. The observed signals may then be modified. Signals from antibody B that is bound to protein B are then generated, followed by observing the generated signals. The observed signals may then be correlated to the detection of sets of protein A and sets of protein B.

One or more of the method steps may be performed manually, or may be automated and performed using automated systems. In some embodiments, all the method steps may be performed using automated systems.

In some embodiments, a device for detection of a plurality of targets in a biological sample that employs the methods of the invention is provided. The device comprises a sample handling system, a reagent dispensing system, a probe cross-linking system, and a signal detection system. The device may be operable to detect the plurality of targets in the biological sample using a method comprising the steps of: contacting the biological sample with a plurality of target-binding probes to form a plurality of target-bound probes, optionally attaching at least one of the plurality of target binding probes to the biological sample via a covalent bond, observing a first set of signals from a first set of the plurality of target-bound probes, modifying the observed signals, generating a second set of signals from a second set of the plurality of target-bound probes, and observing the second set of signals. The sample handling system may comprise a platform for holding the sample (e.g., a microscope stage for holding the tissue section slide), and ports for inputting and outputting one or more reagents to the sample. The sample handling system may further comprise an incubation system that may be used to control the incubation parameters (e.g., temperature, pressure). The sample handling system may be configured as a flow cell, with integrated sample holding platform, integrated ports for reagent inflow and outflow, and/or integrated incubation system. The reagent dispensing system may comprise one or more reagent reservoirs capable of holding one or more reagents, and means of dispensing the reagents to a sample located at the sample handling system. The reagents may be dispensed to the sample via pipetting into a port on the slide holder or via pumping through a tube connecting the slide holder and reagent dispensing system. The signal detection system may comprise a light source (e.g., a microscope light source) and a signal capturing system. For example, the signal detection system may be a microscope having a light source and a camera (e.g., a CCD camera) for digital capturing of the image of the biological sample. The probe cross-linking system may include a light source, which may be controlled to emit a light of specified wavelength for a specified time period. When signal detection system comprises a light source, the probe cross-linking system may be configured to use the same light source. In some embodiments, the probe cross-linking system may be configured to a part of the signal detection system.

The device may be a fully automated (i.e., without any operator intervention) or a semi-automated, wherein at least one of the sample handling system, the probe cross-linking system, the reagent dispensing system, or the signal detection system are operable without operator intervention. The device may comprise a central processing unit, a memory, a controller unit, and/or a display device. The display device may be used to display the observed signal (e.g., images of the biological sample). The controller unit may be capable of communicating with at least one of the central processing unit, the sample handling system, the reagent dispensing system, the probe cross-linking system, or the signal detection system. The communication may be a one-way communication, or a two-way communication. The controller unit may be operable using a pre-determined set of instructions (via an algorithm). While employing two-way communication, the pre-determined set of instruction may be adjusted depending on the feedback from any of the central processing unit, the sample handling system, the reagent dispensing system, the probe cross-linking system, or the signal detection system.

The sample handling system may comprise a platform for holding the biological sample. The platform may be stationary or it may be moved from one location to another for transporting the biological sample. The reagent dispensing system may be used to dispense at least one reagent solution comprising at least one target-binding probe to the biological sample. For example, the reagent dispensing system may be used to dispense a reagent solution comprising a plurality of target-binding probes on to the biological sample for contacting the biological sample with the plurality of target-binding probes. In some embodiments, the reagent dispensing system may be used to dispense multiple reagent solutions (either simultaneously or sequentially), each solution comprising at least one target-binding probe. The reagent dispensing system may also be used to dispense a washing solution that may be used to remove any target-binding probes that are not bound to the target, a blocking solution for blocking the biological sample from non-specific binding, or other reagents that may be necessary for probe cross-linking, washing, and/or signal detection. In some embodiments, the reagent dispensing system may be used dispense a reagent solution comprising a chemical agent for modifying the observed signals for a set of targets.

In some embodiments, a kit for detecting a plurality of multiple targets in a biological sample is provided. The kit may comprise one or more reagents that may be needed to perform the aforementioned methods, packaged together. For example, the kit may comprise a plurality of target-binding probes, and buffers for washing the un-bound target-binding probes. The kit may comprise a target-binding probe, which is capable of generating a signal and is capable of cross-linking to a target or to a molecule that is located in the vicinity of the target, and a chemical agent, capable of modifying the generated signal. In one example, the kit comprises a fluorescent-labeled target-binding probe (e.g., a fluorescent-labeled antibody) that is capable of cross-linking to the biological sample, and a chemical agent capable of destroying the florescence from the fluorescent label. The kit may also contain reagents that may be required for the cross-linking reaction. The kit may further comprise, an instruction manual, detailing the components present in the kit and/or a protocol for carrying out the necessary method steps using the components present in the kit.

In one example, the kit for detection of a plurality of multiple targets in a biological sample comprises a plurality of target-binding probes, wherein each target-binding probe is capable of generating a signal, and at least one of the target-binding probe is capable of cross-linking to its target or to a molecule that is located in the vicinity of the target; and at least one chemical agent, capable of modifying the generated signal from at least one target-binding probe. The plurality of target-binding probes may comprise at least two sets of different target-binding probes that are capable of binding two different targets. For example, the kit may comprise a first set of target-binding probes that specifically binds to compartmental biomarkers (e.g., biomarkers present in the nucleus) and a second set of target-binding probes that specifically binds to a disease marker (e.g., a cancer biomarker). In some embodiments, one single chemical agent may be used to modify the generated signal(s) from all the target-binding probes. However, it may also be possible for the kit to include multiple chemical agents for modifying the signal generated from each target-binding probe in the kit.

The methods facilitate accurate and reliable analysis of a plurality (e.g., potentially infinite number) of targets (e.g., disease markers) from the same biologically sample. The detection of a plurality of targets may find applications in analytic, diagnostic, therapeutic, or prognostic applications in biology and in medicine. For example, the methods for analyzing a cell or a tissue sample from a patient may be employed diagnostically (e.g., to identify patients who have a particular disease, have been exposed to a particular toxin, or are responding well to a particular therapeutic or organ transplant) and prognostically (e.g., to identify patients who are likely to develop a particular disease, respond well to a particular therapeutic or be accepting of a particular organ transplant).

EXAMPLES

Unless specified otherwise, ingredients described in the examples are commercially available from common chemical suppliers. Some abbreviations used in the examples section are expanded as follows: "mg": milligrams; "ng":

nanograms; "pg": picograms; "fg": femtograms; "ag": attograms; "zg": zeptograms; "µL": microliters; "mL": milliliters; "mg/mL": milligrams per milliliter; "mM": millimolar; "µM": micromolar; "pM": picomolar; "nmol": nanomoles; "mmol": millimoles; "pmol": picomoles; "ms": milliseconds; "min.": minutes; "h.": hours, and "° C.": degree Celsius.

FIG. 1 is a flow diagram schematically illustrating the method steps in accordance with one embodiment of the invention. Figure illustrates the detection of two sets of different of targets by simultaneous application of two sets of target-binding probes followed by sequential detection of each set of the target-bound probes. The method comprises the steps of applying a plurality of different target-binding probes to a biological sample (12). The plurality of target-binding probes comprises multiple sets of target-binding probes (e.g., two sets of target-binding probes) that may be detected sequentially. Upon contacting followed by incubation, the plurality of target-binding probes gets bound to the plurality of different targets. The target-binding probes are then cross-linked (covalently attached) to the biological sample (14). The covalent attachment of the target-bound probes to the biological sample may be through the target (i.e., the probes are cross-linked to the target) or through a molecule that is located in the vicinity of the target (e.g., cross-linking of the probe to a nearby protein). Once the plurality of target-binding probes is bound to the plurality of different targets (e.g., two sets of targets), the plurality of targets may be sequentially detected by detecting the plurality of target-bound probes sequentially. If the first set of the plurality of target-bound probes comprises a signal generator, signal(s) from the signal generator may be observed without requiring any additional signal generation steps (20). However, if the first set of the plurality of target-bound probes does not emit a signal by itself, additional steps of signal generation may be required. In one embodiment, this is achieved by associating a signal generator to the first set of the plurality of target-bound probes (18). The signal may then be observed from the first set of the plurality of target-bound probes (20). Once the signal(s) from the first set of the target-bound probes is observed (e.g., by imaging), the observed signal is modified (e.g., removed) (22). The observed signal may be modified by incubating the biological sample with a chemical agent. Once the observed signal from the first set of target-bound probe is modified, a signal is generated from a second set of plurality of target-bound probes (24). The generated signal may then be observed to detect the second set of target-bound probe (26).

Figure 2:
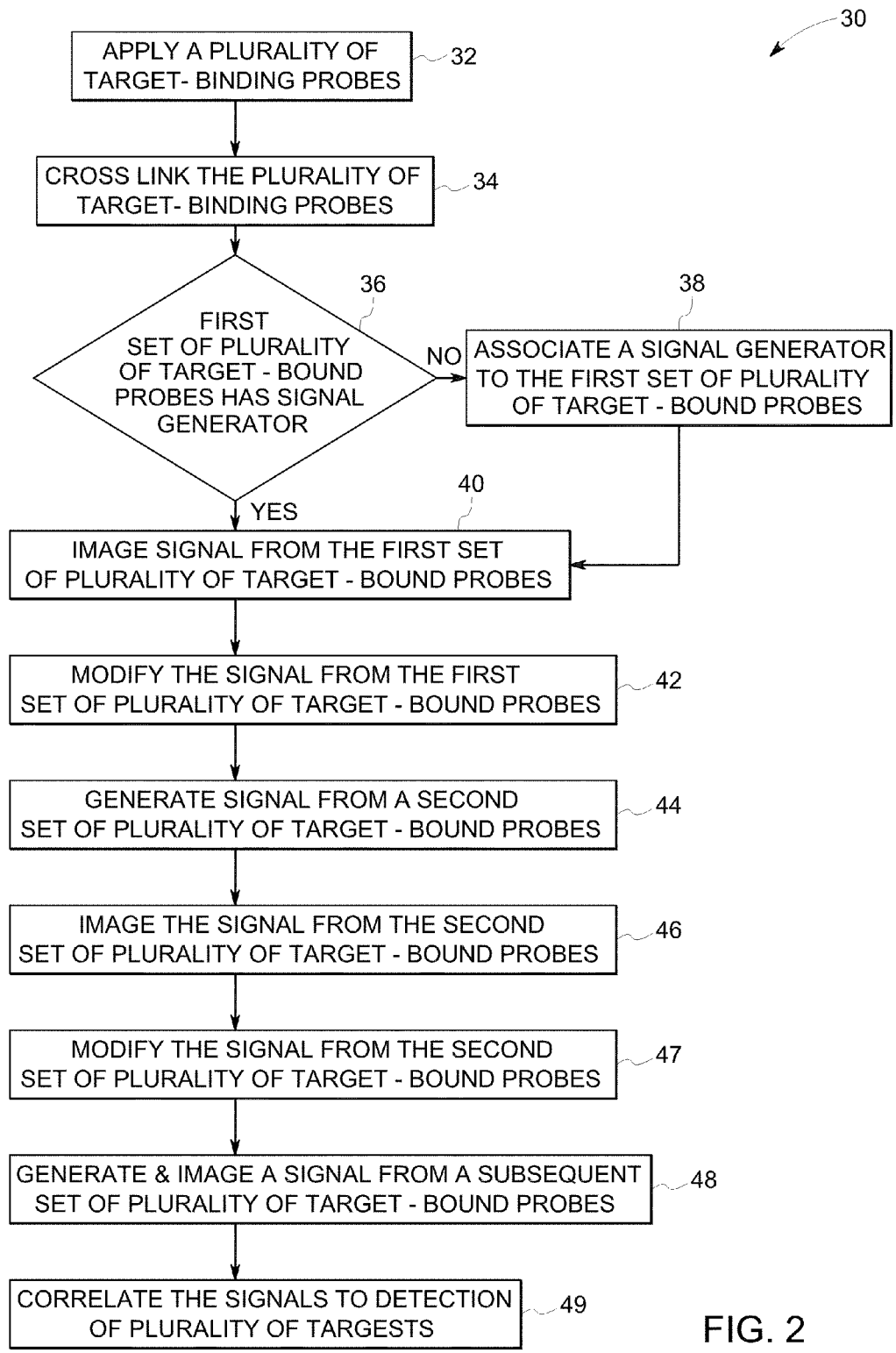
FIG. 2 is a flow diagram illustrating an embodiment of the invention.

FIG. 2 schematically illustrates the method steps in accordance with one embodiment of the invention to detect a plurality of (e.g., $1^{st}$ set, $2^{nd}$ set, and $n^{th}$ set, integer value of "n" may range from 1 to 100) different targets. The method comprises the steps of applying a plurality of different target-binding probes to the biological sample (32). The plurality of target-binding probes comprises multiple sets of target-binding probes (e.g., $1^{st}$ set, $2^{nd}$ set, and $n^{th}$ set, integer value of "n" may range from 1 to 100) that may be detected sequentially. Once the plurality of target-binding probes is bound to the plurality of different targets, the plurality of different targets may be sequentially detected by detecting the plurality of target-bound probes sequentially. Upon contacting the biological sample followed by incubation, the plurality of target-binding probes gets bound to the plurality of different targets. The target-binding probes may then be cross-linked (e.g., covalently coupled) to the biological sample (34). Any of the covalent coupling methods may be used to covalently attach the target-binding probe to the biological sample. For example, the target-binding probe may be covalently coupled to the biological sample via an amide bond, an ester bond, a disulfide bond, a carbon-carbon bond, and the like. If the first set of the plurality of target-bound probes comprises a signal generator, signal(s) from the signal generator may be observed without requiring any additional signal generation steps (40). However, if the first set of the plurality of target-bound probes does not emit a signal by itself, additional steps of signal generation may be required. In one embodiment, this is achieved by associating a signal generator to the first set of the plurality of target-bound probes (38). The signal may then be observed from the first set of the plurality of target-bound probes (40) by imaging the biological sample. Once the signal(s) from the first set of the target-bound probes is observed by imaging, the observed signal is modified (42). A second set of signal(s) is then generated from a second set of plurality of target-bound probes (44). The second set of signal may be or may not be the same as the first set of signals. The second set of signal(s) is then observed by imaging the biological sample (46). Once observed, this second set of signal(s) is modified (e.g., destroyed by applying a chemical agent or photo bleached) (47). The method steps of signal generation, modification, and observation may be repeated multiple times to generate signal from a subsequent set of target-bound probes, and image the subsequent set of target-bound probes (48). The observed signals may then be correlated to the detection of the plurality of targets in the biological sample (49). The correlation step may be performed either immediately after observing each set of signal(s) from each set of target-bound probes or it may be performed after observing all the signal(s) from all the target-bound probes.

Example 1

The cross-linker modified, cyanine dye-labeled, DNA oligomer, Cy3-T20-SFAD was synthesized as follows. A 10 µL (31.9 nmoles) solution of Cy3-T20-NH2 (a thymidine oligomer comprising 20 thymidine units that is labeled with an amino modified linker at the 3'-end and labeled with a Cy3™ dye at the 5'-end, obtained commercially from Integrated DNA technologies, USA) in 10×PBS (Phosphate buffered saline) was diluted with 80 µL water and 10 µL of 1M NaHCO$_3$/Na$_2$CO$_3$ buffer (pH 8.4). To this, a 10 mM DMSO solution (20 equivalents) of sulfosuccinimidyl-[pentafluoroazidobenzamido]ethyl-1,3-dithiopropionate (Sulfo-SFAD, obtained commercially from ThermoFisher Scientific Inc., IL, USA.) was added. The mixed solution was stirred at room temperature for about 1-2 hours. The crude mixture was purified on NAP-10 column (GE Healthcare, USA) using protocol provided by the column supplier.

Sulfo-SFAD is a heterobifunctional cross-linker that contains an amine reactive sulfo-N-hydroxysuccinimide (NHS) ester, and a photoactivable tetrafluorophenyl azide at opposite ends of a disulfide spacer arm having a length of 14.6 Å. NHS ester reacts efficiently with primary amino groups in pH 7-9 buffers to form a stable amide bond. When exposed to UV light (300-370 nm), perfluorophenyl azide forms an extremely reactive nitrene group that can insert into active carbon-hydrogen bonds (C—H) or add to unsaturated carbon chains. The perfluoroaryl nitrene reacts quickly and nonspecifically inserts in C—H bonds with greater efficiency than non-fluorinated aryl azides.

Example 2

The cross-linker modified, cyanine dye-labeled, DNA oligomer, Cy3-T20-SDAD was synthesized as follows. A 10

μL (31.9 nmol) solution of Cy3-T20-NH2 (a thymidine oligomer comprising 20 thymidine units that is labeled with an amino modified linker at the 3'-end and labeled with a Cy3™ dye at the 5'-end, obtained commercially from Integrated DNA technologies, USA) in 10×PBS (Phosphate buffered saline) was diluted with 80 μL it water and 10 μL of 1 M NaHCO$_3$/Na$_2$CO$_3$ buffer (pH 8.4). To this, a 10 mM aqueous solution (20 equivalents) of sulfosuccinimidyl 2-([4,4'-azipentanamido]ethyl)-1,3'-dithiopropionate (Sulfo-SDAD, obtained commercially from ThermoFisher Scientific Inc., IL, USA.) was added. The mixed solution was stirred at room temperature for 1-2 hours. The crude mixture was purified on NAP-10 column (GE Healthcare, USA) using protocol provided by the column supplier.

Sulfo-SDAD is a heterobifunctional cross-linker that contains an amine reactive sulfo-N-hydroxysuccinimide (NHS) ester, and a photoactivable diazirine moiety at opposite ends of a disulfide spacer arm having a length of 13.5 Å. NHS ester reacts efficiently with primary amino groups in pH 7-9 buffers to form a stable amide bond. Photoactivation of diazirine with long-wave UV light (330-370 nm) creates reactive carbene intermediates. Such intermediates can form covalent bonds through addition reactions with any amino acid side-chain or peptide backbone at distances corresponding to the spacer arm lengths.

Example 3

The cross-linker modified, cyanine dye-labeled, DNA oligomer, Cy3-T20-SANPAH was synthesized as follows. A 10 μL (31.9 nmol) solution of Cy3-T20-NH2 (a thymidine oligomer comprising 20 thymidine units that is labeled with an amino modified linker at the 3'-end and labeled with a Cy3™ dye at the 5'-end, obtained commercially from Integrated DNA technologies, USA) in 10×PBS (Phosphate buffered saline) was diluted with 80 μL water and 10 μL of 1M NaHCO$_3$/Na$_2$CO$_3$ buffer (pH 8.4). To this, a 20 mM aqueous solution (50 equivalents) of N-sulfosuccinimidyl-6-(4'-azido-2'-nitrophenylamino) hexanoate (Sulfo-SANPAH, obtained commercially from ThermoFisher Scientific Inc., IL, USA.) was added. The mixed solution was stirred at room temperature for 1-2 hours. The crude mixture was purified on NAP-10 column (GE Healthcare, USA) using protocol provided by the column supplier.

Sulfo-SANPAH is water soluble, heterobifunctional cross-linker with a spacer arm length of 18.2 Å. The Sulfo-SANPAH cross-linking reagent contains an NHS ester that reacts with primary amines and a nitrophenylazide group that is photo reactive at 320-350 nm.

Example 4

The cross-linking of DNA probes to a protein was investigated by contacting cyanine-dye labeled, DNA oligomers (Cy3-T20-SFAD or Cy3-T20-SDAD) having cross-linking functionalities with streptavidin. Cy3-T20-SFAD and Cy3-T20-SDAD differ from each other only in their cross linking functionalities. The cyanine-dye labeled, DNA oligomer having no cross-linking functionality, Cy3-T20-NH2 served as control. The reaction was performed in triplicates, with two sets of experiments for each oligomer (i.e., two sets of three wells/oligomer). For each reaction, Cy3-labeled oligomers (100 μL/well, 1 μM or 0.1 μM) were added to streptavidin-coated wells in a microtiter plate (Reacti-Bind (high binding capacity) plates, obtained commercially from ThermoFisher Scientific, IL, USA.). One set (for each oligomer, in triplicates) was exposed to UV light for 20 minutes, while other set (for each oligomer, in triplicates) was kept in the dark. After the reaction, excess reagents were removed, and wells were washed with 1×PBS thrice. The wells were then replenished with 100 μL 1×PBS, and the microtiter plate was read on a Tecan plate reader (Excitation wavelength was 544 nm and emission wavelength was 595 nm). Each set was performed with two different concentration of each oligomer (1 μM and 0.1 μM), and relative fluorescence counts were compared.

Figure 3:
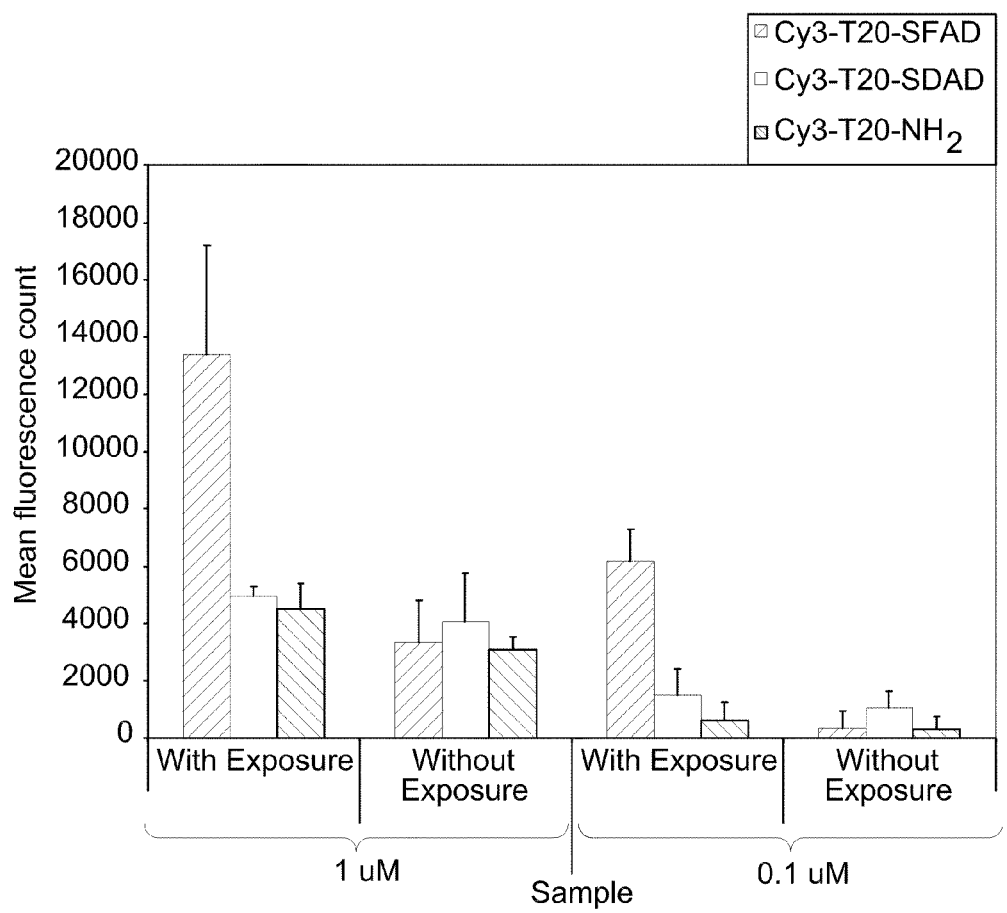
FIG. 3 shows cross-linking of cyanine-dye labeled, DNA oligomers (Cy3-T20-SFAD or Cy3-T20-SDAD) to streptavidin-coated plates.

FIG. 3 shows the mean fluorescence count for each set at two different concentrations of Cy3-T20-SFAD and Cy3-T20-SDAD. FIG. 3 shows significant cross-linking of the Cy3-T20-SFAD oligomer to streptavidin upon exposure to UV light. 0.44% of Cy3-T20-SFAD was cross-linked to streptavidin when 1 μM of Cy3-T20-SFAD was used for the experiment. When a concentration of 0.1 μM was used, 0.15% of Cy3-T20-SFAD was cross-linked to streptavidin. When conducted in the dark (control), the cross linking of Cy3-T20-SFAD was reduced considerably. Control oligomer and Cy3-T20-SDAD did not show significant differences between UV exposed and unexposed samples.

Example 5

The cross-linking of DNA probes with cells was studied by incubating cyanine-dye labeled, DNA oligomers (Cy3-T20-SANPAH, or Cy3-T20-NH2 (Control)) with cells. Cy3-T20-SANPAH includes an azide functional group that may react (and thus cross-link the probes) with the cellular proteins. The control probe, Cy3-T20-NH2, does not contain any cross-linking functionalities.

The reaction was performed with two sets for each oligomer at 25 nM concentration. The LNCap (androgen-sensitive human prostate adenocarcinoma cells) pellet slides (obtained commercially from Cell Signaling Technology Inc., MA, USA.) were de-waxed and antigens were retrieved on the Ventana autostainer employing Ventana Discovery system's protocol for dewaxing and two-step medium antigen retrieval protocol. Slides were washed with detergent (once), water (thrice) and 1×PBS (once). For each reaction, 300 μL it of oligomer solution was placed on each slide, and slides were incubated in dark for 1 h. One set (for each oligomer) was exposed to UV light (a transilluminator) for 40 minutes, while other set (for each oligomer) was left in the dark. After the reaction, excess reagents were removed, and slides were washed with 1×PBS for 10 min. The slides were further washed with 1×PBS and stained with DAPI (1 μg/mL, 2.86 μM) for 5 min Slides were then removed from DAPI solution, mounted using Vectashield, and imaged. Imaging was performed using Zeiss imager using Cy3 exposure of 20 ms.

Figure 4:
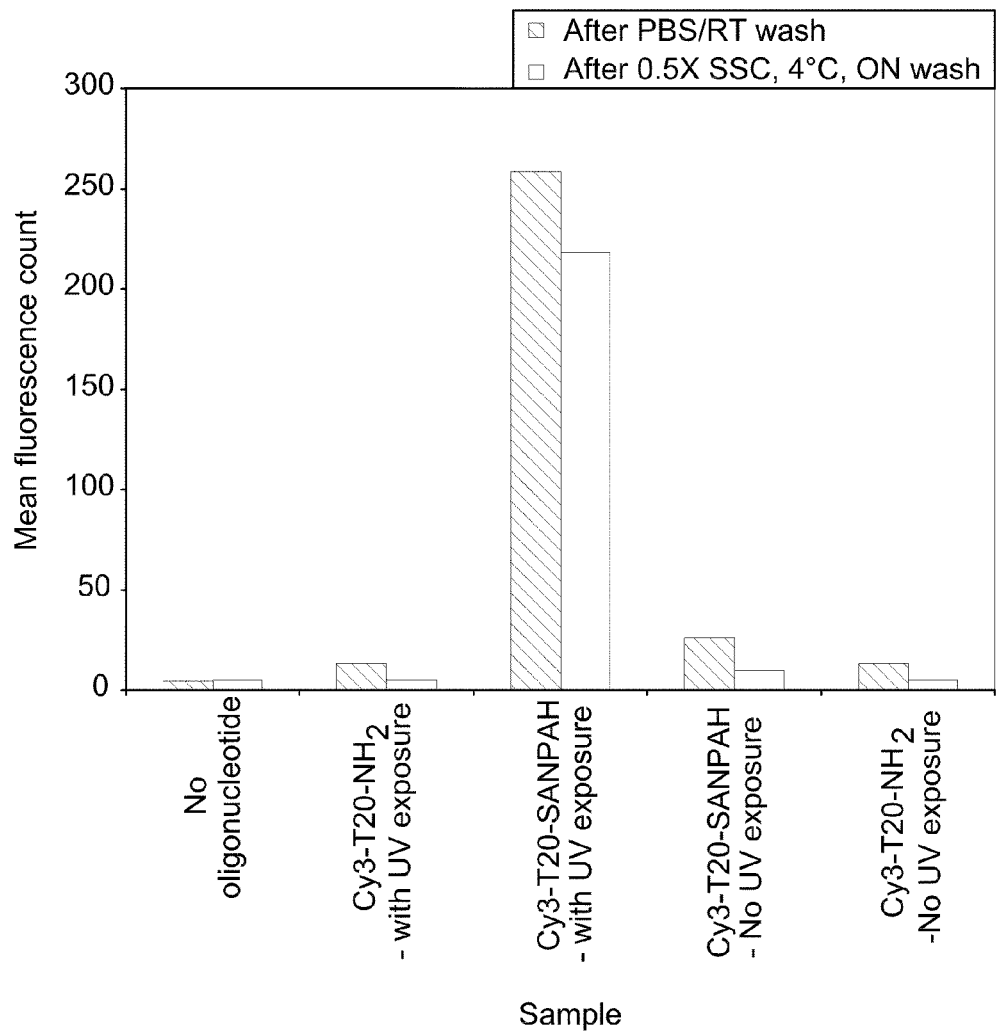
FIG. 4 shows interaction of cyanine-dye labeled, DNA oligomers (Cy3-T20-NH2 or Cy3-T20-SANPAH) to cells.

FIG. 4 shows the mean fluorescence count for each set. Slides incubated with Cy3-T20-SANPAH under UV light showed a higher fluorescent count compared to the rest. This clearly indicates that the oligomer, Cy3-T20-SANPAH cross-linked with cells upon UV exposure. Faint stains were observed in other sets. Coverslips were removed by placing slides in 1×PBS, and the slides were incubated with 0.5× SSC at 40° C. overnight. After washing with 1×PBS (ON wash), slides were mounted and imaged on Ziess. Cy3 exposure time was kept at 20 ms. FIG. 4 shows the mean fluorescence count for each set. FIG. 4 clearly shows that only the slide with cross-linker conjugated oligomer and exposure to light exhibits good signals. Quantitative analysis confirms this.

Example 6

Multiplexed detection of poly(A) mRNA and U6 snRNA probes in a tissue sample was performed by simultaneous addition of target-binding probes followed by sequential detection of target-bound probes as follows. 5'-biotin-labeled LNA™ mRNA in situ hybridization probe, PolyT(25)Vn (commercially obtained from Exiqon, USA) and 5'-digoxygenin-labeled miRCURY LNA™ detection probe, U6 hsa/mmu/rno (commercially obtained from Exiqon, USA) were used for detecting total poly(A) mRNA and the U6 snRNA probes respectively. A slide containing human colon cancer tissue sample was de-waxed in histochoice (commercially obtained from AMRESCO, USA), and rehydrated in decreasing amounts of ethanol for 15 minutes. The tissue sample was then washed in 1×PBS, 0.3% Triton X-100 in 1×PBS (wt/wt %), followed by 1×PBS. The tissue sample was then dehydrated for 10 minutes each in 50%, 70%, 95% and 100% ethanol (v/v % in water), and was air-dried for 20 minutes. A solution containing PolyT(25)Vn and U6 hsa/mmu/rno (25 nM) in hybridization buffer (50% Formamide, 2×SSC, 500 ug/ml yeast tRNA, 0.1% Tween-20) was applied. The probes were heated in a temperature block at 95° C. for 10 minutes, briefly centrifuged, and applied to the tissue sample. Tissue sample was then covered with a cover glass, and sealed. The slide was then incubated for 12 h at 37° C. in a humidified chamber. Following hybridization, the tissue sample was washed in 2×SSC for 5 minutes, 0.5×SSC for 5 minutes, and 0.5×SSC for 10 minutes at 67° C.

Figure 5:
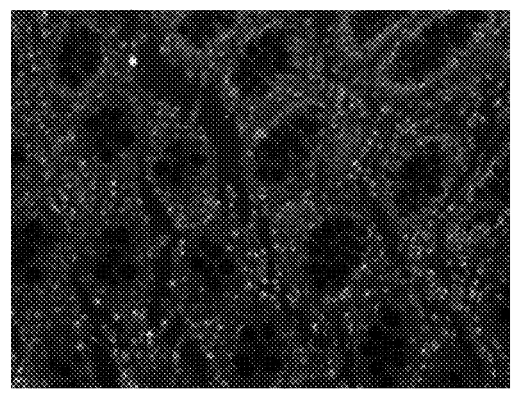
FIG. 5 depicts images showing multiplexed detection of poly(A) mRNA and U6 snRNA probes in a tissue sample by simultaneous addition of probes followed by sequential detection of target-bound probes.
Figure 5:
Figure 5:
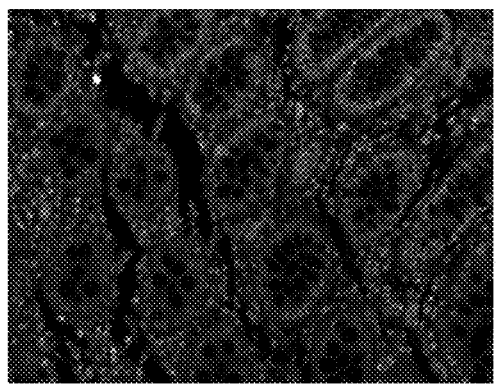

The tissue sample then washed with 1×PBS, and incubated with Cy3-labeled streptavidin (Jackson Immunolabs, USA) in 3% BSA PBS (wt/wt %) for 30 minutes at room temperature, and imaged on a Zeiss microscope using Cy3 filter cubes. FIG. 5 (sample 1) shows a strong signal in Cy3 channel indicating the detection of poly(A) mRNA. Following the detection of poly(A) mRNA, the slide was treated with basic 3% $H_2O_2$ in 200 mM $NaHCO_3$ (chemical bleaching solution) for 15 minutes. The slide was rinsed in 1×PBS, once again treated with 3% $H_2O_2$ in 200 mM $NaHCO_3$ for 20 minutes, followed by rinsing with 1×PBS. The slide was then imaged in all channels. FIG. 5 (sample 2) shows that the most of Cy3 signal was bleached upon treatment with the chemical bleaching solution. Finally, the slides were incubated with Rhodamine-labeled anti-digoxigenin antibody (Roche, USA) to detect the U6 transcript. The slide was observed by imaging using Cy3 filter cubes. FIG. 5 (sample 3) shows a strong signal in Cy3 channel (Rhodamine fluorescence overlap with Cy3 fluorescence) indicating the detection of U6 snRNA transcript. The digoxygenin labeled U6. hsa/mmu/rno probe was retained in the sample even after the tissue sample was subjected to the chemical bleaching.

Example 7

Cross-linker modified, cyanine labeled 5'-Cy3-b-actin-LNA-AmM-SANPAH (illustrated in structure 1; star sign (*) after a nucleotide symbol indicates that the nucleotide is a locked nucleic acid (LNA) nucleotide) is synthesized as follows.

Structure 1

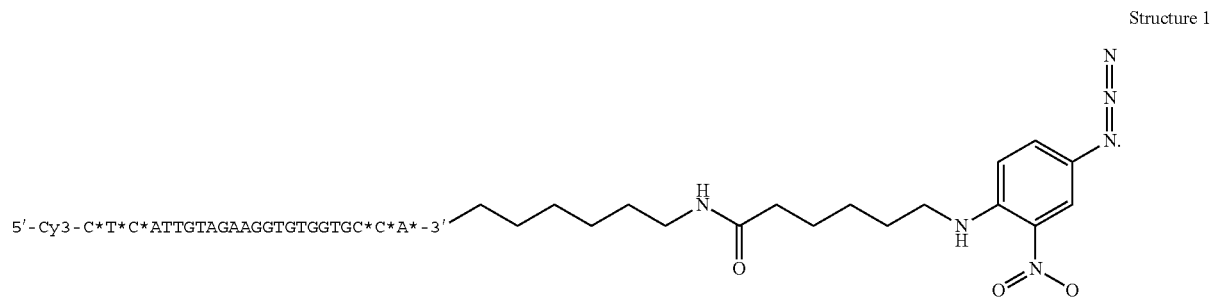

A 20 µL (14.13 nmole) solution of 5'-Cy3-b-actin-LNA-AmM oligonucleotide in 5×PBS was mixed with 70 µL water and 10 µL of 1 M $NaHCO_3/Na_2CO_3$ (pH 8.4) buffer. A 20 mM solution of Sulfo-SANPAH (ThermoFischer Scientific Inc., IL, USA.) was prepared by dissolving 2 mg of sulfo-SANPAH in 203 µL water. 35.3 µL (50 equivalents) of this solution was added to the oligonucleotide solution with stirring. After 2 hours of stirring in the dark, the mixture was stored in the refrigerator for 12 h. Purification was performed on PD-10 column (GE Healthcare, USA) using manufacturer's protocol. Pink colored material was collected (in fraction 1) and was analyzed by HPLC. Main peak corresponded to the product (purity ~91%) and unmodified oligonucleotide was the main impurity.

Example 8

Cross-linker modified, biotin labeled 5'-Biotin-U6-LNA-AmM-SANPAH (illustrated in structure 2; star sign (*) after a nucleotide symbol indicates that the nucleotide is a locked nucleic acid (LNA) nucleotide) is synthesized as follows.

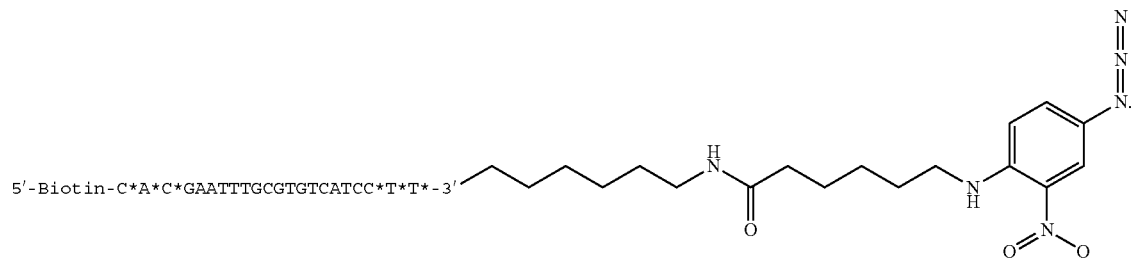

Structure 2

A 20 μL (22.04 nmole) solution of 5'-Biotin-U6-LNA-AmM oligonucleotide in 5×PBS was mixed with 70 μL water and 10 μL of 1 M NaHCO$_3$/Na$_2$CO$_3$ (pH 8.4) buffer. A 20 mM solution of sulfo-SANPAH (from ThermoFischer Scientific Inc. IL, USA.) was prepared by dissolving 2 mg of sulfo-SANPAH in 203 μL water. 55.1 μL (50 equivalents) of this solution was added to the oligonucleotide solution with stirring. After 2 hours of stirring in the dark, mixture was stored in the refrigerator for 12 h. Purification was performed on PD-10 column using manufacturer's protocol. The colorless material was collected (in fraction 1) and was analyzed by HPLC. Only one peak was observed, and that corresponded to the desired product.

Example 9

Figure 6:
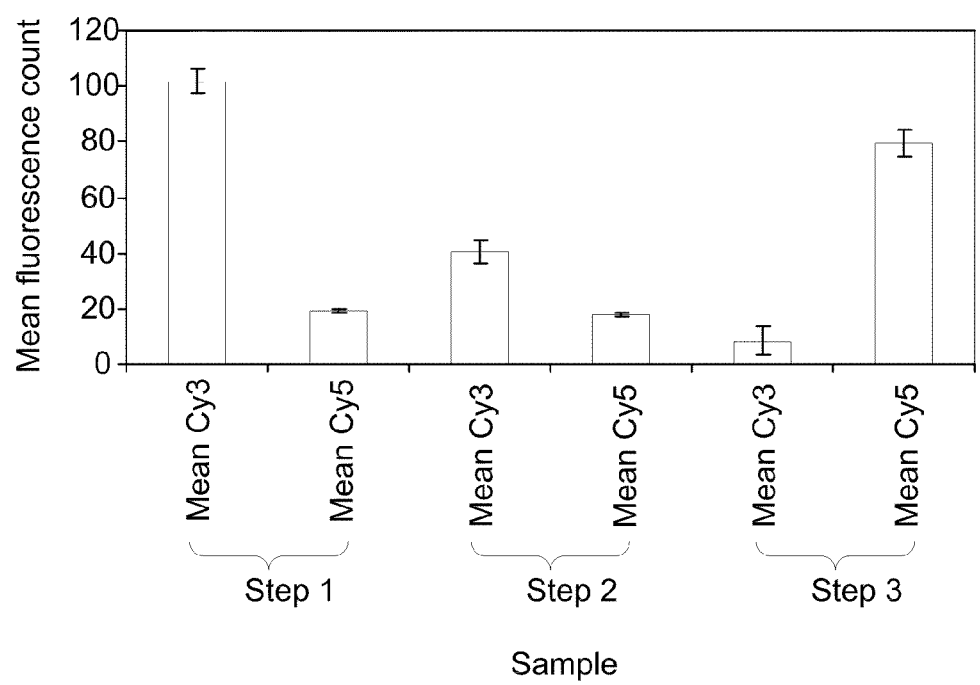
FIG. 6 shows multiplexed detection of b-actin and U6 probes in a tissue sample by simultaneous addition of probes followed by cross-linking, and sequential detection of target-bound probes.

Multiplexed detection of b-Actin and U6 probes in a tissue sample was performed by simultaneous addition of probes, 5'-Cy3-b-actin-LNA-AmM-SANPAH and 5'-Biotin-U6-LNA-AmM-SANPAH, followed by cross-linking of the probes, and their sequential detection as follows. A slide containing human tonsil tissue was de-waxed in histochoice (AMRESCO, USA), and then re-hydrated in decreasing amounts of ethanol and triton X-100 (0.3% in PBS) for 15 minutes. The tissue was then washed in 1×PBS. A solution containing 5'-Cy3-b-actin-LNA-AmM-SANPAH and 5'-Biotin-U6-LNA-AmM-SANPAH probes (25 nM each) in hybridization buffer (2×SSC/50% formamide/5% dextran sulfate) was applied. The probes were cross-linked with the tissue for 40 minutes using DR180 transilluminator at room temperature. Slides were then washed in 1×PBS, stained with DAPI, and imaged on a Zeiss microscope using Cy3, Cy5 & DAPI cubes. FIG. 6 shows a strong signal was observed in Cy3 channel indicating the presence of b-actin probe (step 1). As expected, no signal other than a weak sample autofluorescence was present in Cy5 channel. Following observation of b-actin probe, slide was treated with basic 3% H$_2$O$_2$ in 200 mM NaHCO$_3$ for 20 minutes. The slide was rinsed in PBS, and was once again treated with 3% H$_2$O$_2$ in 200 mM NaHCO$_3$ for 20 minutes, followed by rinsing with PBS. Images were then recorded in all channels. The images showed the bleaching of most Cy3 signal (step 2). Some residual signals were observed, may be due to endogenous autofluorescence or incomplete bleaching. Finally, the slides were incubated with Cy5-labeled streptavidin to detect U6 probe (via detection of the U6-bound biotinylated probe 5'-Biotin-U6-LNA-AmM-SANPAH probes). The slide was observed by imaging. Imaging showed a strong signal in Cy5 channel (step 3) indicating that biotinylated probe was retained in the sample even after the sample was subjected to a bleaching cycle.

Figure 7:
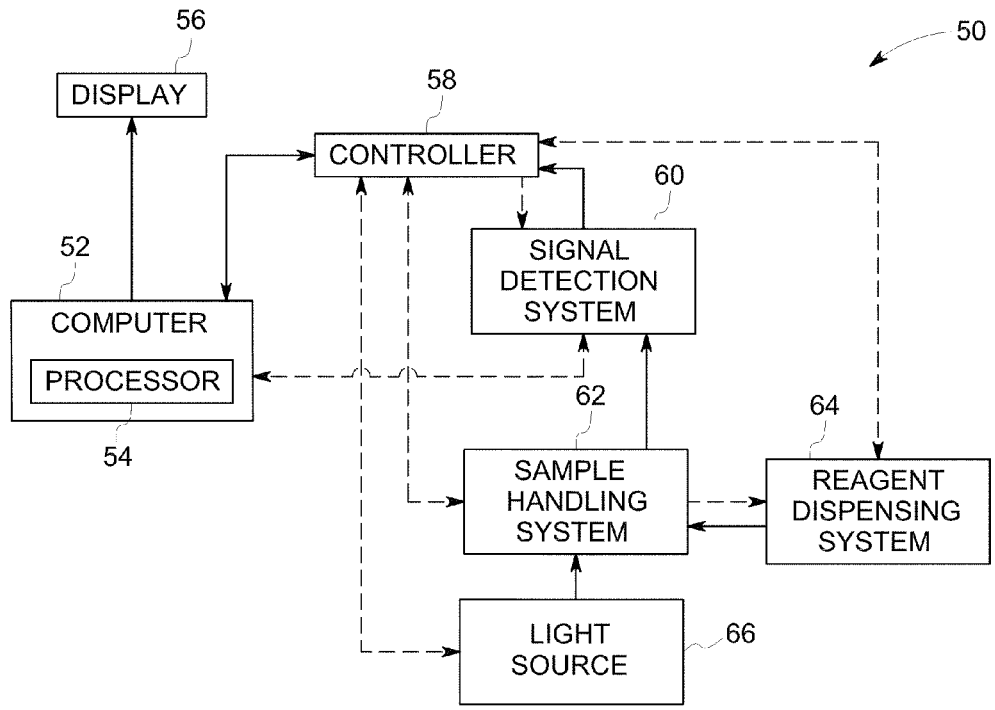
FIG. 7 is a block diagram, schematically illustrating an exemplary device according to one embodiment of the invention.

FIG. 7 is a block diagram of a device (50) for detecting a plurality of different targets in a biological sample according to one embodiment of the invention. The device comprises a sample handling system (62), a reagent dispensing system (64), a light source (66), and a signal detection system (60). The light source may act as a probe cross-linking system as well as a light source for the signal detection system. The illustrated device (50) further comprises a computer (52) having a memory and a processor (54), a controller unit (58), and a display device (56). In the figure, arrows indicate communication links, double-headed arrows depict mutual communication links, and dotted arrows indicates optional communication links.

The controller unit is capable of communicating with at least one of the computer (52), the sample handling system (62), the reagent dispensing system (64), the light source (66), or the signal detection system (60). The communication may be a one-way communication, or a two-way communication. The sample handling system (62), the light source (66), the reagent dispensing system (64) and the signal detection system (60) may be controlled by the controller unit (58), which control signals/protocols for detection of multiple targets. Moreover, the signal detection system (60) is coupled to the controller (58), which may command acquisition of the signals. The controller 58 may also execute various functions, such as for initial adjustment of sample handling system (62), light source (66), and so forth. In general, controller (58) commands operation of the device to execute the steps of the method for detecting multiple targets and to process acquired data. Controller (58) may also include signal processing circuitry, typically based upon a general purpose or application-specific digital computer, associated memory circuitry for storing programs and routines executed by the computer, and so forth.

The computer (52) typically is coupled to, or incorporates the controller (58). The data collected by the signal detection system (60) may be transmitted to the computer (52) for subsequent processing and reconstruction either directly or through the controller (58). The computer (52) may include or communicate with a memory that can store data processed by the computer (52) or data to be processed by the computer (52). It should be understood that any type of memory configured to store a large amount of data might be utilized by such an exemplary system 50. Moreover, the memory may be located at the device or may include remote components, such as network accessible memory media, for storing data, processing parameters, and/or routines for implementing the methods.

Figure 8:
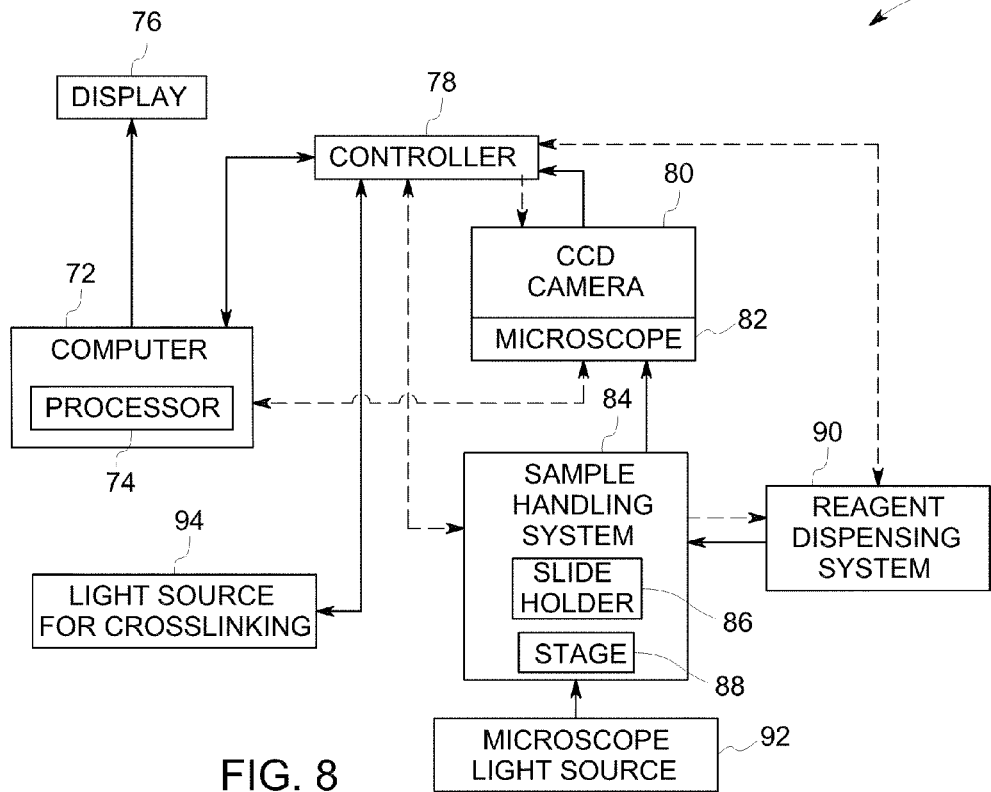
FIG. 8 is a block diagram, schematically illustrating an exemplary histopathology system according to one embodiment of the invention.

FIG. 8 is a block diagram an exemplary histopathology device (70) for detecting a plurality of different targets in a biological sample. The histopathology device comprises a sample handling system (84) having a slide holder (86) and a stage (88), a reagent dispensing system (90), a light source for cross-linking (94), and a signal detection system comprising a microscope (82) and a CCD camera (80). The device may further comprise a computer (72) having a central processing unit (74) and a memory, a controller unit (78), and a display device (76). The controller unit may be capable of communicating with at least one of the central processing unit, the sample handling system, the reagent dispensing system, the probe cross-linking system, or the signal detection system. The communication may be a one-way communication, or a two-way communication.

The computer (72) may also be adapted to control features such as reagent dispensing, probe cross-linking and signal detection that may be enabled by the controller (78). Furthermore, the computer (72) may be configured to receive commands and other parameters from an operator via an operator workstation (not shown), which is typically equipped with a keyboard and other input devices (not shown). An operator may thereby control the system 70 via the input devices. Thus, the operator may observe a reconstructed image/data or other data relevant to the system (70) from the computer (72), initiate imaging, and so forth.

The display (76) coupled to the operator workstation or computer (72) may be utilized to observe the detected signals or reconstructed images. Additionally, the reconstructed images may also be printed by a printer (not shown), which may be coupled to the operator workstation. The display (72) and the printer may also be connected to the computer (72), either directly or via the operator workstation. The operator workstation may also be coupled to a picture archiving and communications system. It should be noted that the operator workstation might be coupled to a remote system, such as histopathology department information system, hospital information system, or to an internal or external network, so that others at different locations may gain access to the reconstructed image.

It should be further noted that the computer (72) and operator workstation might be coupled to other output devices, which may include standard or special purpose computer monitors and associated processing circuitry. One or more operator workstations may be further linked in the system for outputting system parameters, viewing images, and so forth. In general, displays, printers, workstations, and similar devices supplied within the device may be local to the device, or may be remote from the device, such as elsewhere within an institution or hospital, or in an entirely different location, linked to the signal detection system via one or more configurable networks, such as the Internet, a virtual private network or the like.

The foregoing examples and embodiments are illustrative of some features of the invention rather than limiting on the invention described herein. They are selected embodiments or examples from a manifold of all possible embodiments or examples. The invention may be embodied in other specific forms without departing from the spirit or essential characteristics thereof. It is, therefore, to be understood that the appended claims are intended to cover all modifications and changes that fall within the true spirit of the present invention.

The invention claimed is:

1. A method of detecting at least three sets of different targets in a biological sample via simultaneous addition of at least three sets of different target-binding probes followed by their sequential detection, the method comprising:

(a) simultaneously contacting the at least three sets of different targets with the at least three sets of different target-binding probes to form a plurality of target-bound probes;

(b) covalently attaching each of the plurality of target-bound probes of step (a) to the corresponding target or to a molecule that is located in the vicinity of the corresponding target in the biological sample to form a plurality of covalently attached probes; and (c) sequentially detecting the plurality of covalently attached probes of step (b) to sequentially detect each set of different target, wherein the sequential detection comprises:

(i) generating a first set of signals from a first set of probes in the plurality of covalently attached probes by contacting a first set of signal-generating probes that are capable of binding to the first set of probes;

(ii) detecting a first set of targets via observing the first set of signals that is generated in step (i);

(iii) modifying the observed first set of signals by applying a chemical agent after step (ii);

(iv) generating a second set of signals after step (iii) from a second set of probes in the plurality of covalently attached probes by contacting a second set of signal-generating probes that are capable of binding to the second set of probes;

(v) detecting a second set of targets via observing the second set of signals that is generated in step (iv);

(vi) modifying the observed second set of signals by applying a chemical agent after step (v); and (vii) generating a subsequent set of signals from a subsequent set of probes in the plurality of covalently attached probes, detecting a subsequent set of targets via observing the subsequent set of signals, modifying the observed subsequent set of signals by applying a chemical agent, and repeating these steps till all sets of different targets are detected.

2. The method of claim 1, wherein the signal generation, the target detection via signal observation and the signal modification steps in step (vii) are performed on a third, a fourth, and an $n^{th}$ set of the plurality of covalently attached probes using a third, a fourth, and an $n^{th}$ set of signal-generating probes to observe a third, a fourth, and an nth set of signals and thereby to detect a third, a fourth, and an nth set of targets, wherein integer value of n ranges from 5 to 100.

3. The method of claim 1, further comprising imaging the biological sample to obtain a background signal signature prior to generating the first set of signals.

4. The method claim 3, further comprising subtracting the background signal signature from the signals observed in the subsequent signal observing steps.

5. The method of claim 1, further comprising steps for removing the target-binding probes that are not bound to the targets prior to step (b).

6. The method of claim 5, further comprising steps for removing the first set of signal-generating probes that are not bound to the first set of probes in the plurality of covalently attached probes, prior to detecting the first set of targets.

7. The method of claim 1, wherein the targets are selected from the group consisting of a deoxyribonucleic acid, a ribonucleic acid, a protein, and a combination thereof.

8. The method of claim 1, wherein the at least three sets of different targets consist essentially of at least three sets of different ribonucleic acids.

9. The method of claim 1, wherein at least four sets of different targets are detected by simultaneously contacting with at least four sets of different target-binding probes.

10. The method of claim 1, wherein the chemical agent is selected from the group consisting of an acid, a base, a nucleophile, an electrophile, an oxidizing agent, a reducing agent and combinations thereof.

11. The method of claim 1, wherein the first set of signal-generating probes, the second set of signal-generating probes and the subsequent set of signal-generating probes are cyanine dyes.

* * * * *